US006312686B1

(12) United States Patent
Staddon et al.

(10) Patent No.: US 6,312,686 B1
(45) Date of Patent: Nov. 6, 2001

(54) MODULATING THE PERMEABILITY OF A PHYSIOLOGICAL BARRIER WITH AN AGENT THAT MODULATES TYROSINE PHOSPHORYLATION

(75) Inventors: James Martin Staddon; Lee Laurence Rubin, both of London; Kurt Herrenknecht, Harpenden; Mary Louise Morgan, London, all of (GB)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 08/648,182

(22) PCT Filed: Nov. 18, 1994

(86) PCT No.: PCT/GB94/02543

§ 371 Date: Dec. 23, 1997

§ 102(e) Date: Dec. 23, 1997

(87) PCT Pub. No.: WO95/13820

PCT Pub. Date: May 26, 1995

(30) Foreign Application Priority Data

Nov. 19, 1993 (GB) .................................................. 9323884

(51) Int. Cl.[7] .............................. A61K 33/24; C12N 9/99

(52) U.S. Cl. ............................. 424/94.1; 435/194; 514/2; 930/250

(58) Field of Search ........................... 424/94.1; 435/194; 930/250

(56) References Cited

U.S. PATENT DOCUMENTS 5,155,031 10/1992 Posner et al. .......................... 435/184

FOREIGN PATENT DOCUMENTS

| 4-13631 | 1/1992 | (JP) . |
| WO 91/04745 | 4/1991 | (WO) . |

OTHER PUBLICATIONS

Filson et al. Cell Growth and Differentiation. 1 (12) 661–8, Dec. 1990.*
Volberg et al. EMBO Journal, 11, 1733–1742, Sep. 1992.*
Crow et al. Oncogene, 7, 999–1003, May 1992.*
Swenson et al. Cell Regulation, 1, 989–1002, Dec. 1990.*
Lum et al. Can. J. Physiol. Pharmacol., 74, 787–800, May 1996.*
Database BIOSIS, BA88:132304. Uehara, Y. et al. Biochem. Biophys. Res. Commun.163 (2), 803–809, Feb. 1989.*
Galaktionov, K., and Beach, D., "Specific activation of cdc25 tyrosine phosphatases by B–type cyclins: evidence for multiple roles of mitotic cyclins," *Cell* 67:1181–1194 (1991).*
Izumi, T., et al., "Periodic changes in phosphorylation of the Xenopus cdc25 phosphatase regulate its activity," *Mol. Biol. Cell* 3:927–939 (1992).*

Liebow, C., et al., "Somatostatin analogues inhibit growth of pancreatic cancer by stimulating tyrosine phosphatase," *Proc. Natl. Acad. Sci. USA* 86:2003–2007 (1989).*
Mullin, J.M., et al., "Modulation of tumor necrosis factor–induced increase in renal (LLC–PK$_1$) transepithelial permeability," *Am. J. Physiol.* 263:F915–F924 (1992).
Peralta Soler, A., et al., "Tissue remodeling during tumor necrosis factor–induced apoptosis in LLC–PK$_1$ renal epithelial cells," *Am. J. Physiol.* 270:F8690–F879 (May 1996).
Anderson, J.M., et al., "The Structure and Regulation of Tight Junctions," *Curr. Opin. Cell Biol.* 5(5):772–778 (Oct. 1993).
Balda, M.S., et al., "Assembly of the Tight Junction: The Role of Diacylglycerol," *J. Cell Biol.* 123(2):293–302 (Oct. 1993).
Behrens, J., et al., "Loss of Epithelial Differentiation and Gain of Invasiveness Correlates with Tyrosine Phosphorylation of the E–Cadherin/β–Catenin Complex in Cells Transformed with a Temperature–sensitive v–SRC Gene," *J. Cell Biol.* 120(3):757–766 (Feb. 1993).
Citi, S., "Protein Kinase Inhibitors Prevent Junction Dissociation Induced by Low Extracellular Calcium in MDCK Epithelial Cells," *J. Cell Biol.* 117:169–178 (1992).
Citi, S., et al., "The Role of Phosphorylation in the Assembly and Disassembly of Epithelial Junctions," *Molec. Biol. Cell* 3(Suppl.):218a, Abstract No. 1262 (1992).
Collares–Buzato, C.B., et al., "Junctional Uvomorulin/E–cadherin and Phosphotyrosine–modified Protein Content are Correlated with Paracellular Permeability in Madin–Darby Canine Kidney (MDCK) Epithelia," *Histochem.* 101:185–194 (Mar. 1994).
Downing, J.R., and Reynolds, A.B., "PDGF, CSF–1, and EGF Induce Tyrosine Phosphorylation of p120, a pp60$^{src}$ Transformation–associated Substrate," *Oncogene* 6:607–613 (1991).
Durieu–Trautmann, O., et al., "Nitric Oxide and Endothelin Secretion by Brain Microvessel Endothelial Cells: Regulation by Cyclic Nucleotides," *J. Cell. Physiol.* 155(1):104–111 (Apr. 1993).
Fantus, I.G., et al., "Pervanadate [Peroxide(s) of Vanadate] Mimics Insulin Action in Rat Adipocytes via Activation of the Insulin Receptor Tyrosine Kinase," *Biochemistry* 28:8864–8871 (1989).

(List continued on next page.)

*Primary Examiner*—Michael Borin
(74) *Attorney, Agent, or Firm*—Sterne, Kessler, Goldstein & Fox P.L.L.C.

(57) ABSTRACT

Permeability of the blood–brain barrier and other physiological barriers can be modulated by the degree of tyrosine phosphorylation of proteins. Agents which promote tyrosine protein dephosphorylation reduce the permeability of the blood–brain barrier and those which promote phosphorylation increase permeability. Increasing blood–brain barrier permeability is useful in delivering drugs having a desired effect upon the central nervous system; decreasing blood–brain barrier permeability and other physiological barrier permeability is useful in preventing undesired compounds reaching the CNS and in certain clinical conditions.

13 Claims, 20 Drawing Sheets

OTHER PUBLICATIONS

Garcia–Morales, P., et al., "Tyrosine Phosphorylation in T Cells is Regulated by Phosphatase Activity: Studies with Phenylarsine Oxide," *Proc. Natl. Acad. Sci. USA* 87:9255–9259 (1990).

Gumbiner, B., and Simons, K., "A Functional Assay for Proteins Involved in Establishing an Epithelial Occluding Barrier: Identification of a Uvomorulin–like Polypeptide," *J. Cell Biol.* 102:457–468 (1986).

Gumbiner, B., et al., "The Role of the Cell Adhesion Molecule Uvomorulin in the Formation and Maintenance of the Epithelial Junctional Complex," *J. Cell Biol.* 107:1575–1587 (1988).

Hamaguchi, M., et al., "p60$^{v-src}$ Causes Tyrosine Phosphorylation and Inactivation of the N–Cadherin–Catenin Cell Adhesion System," *EMBO J.* 12(1):307–314 (Jan. 1993).

Hedrick, L., et al., "Cell Adhesion Molecules as Tumour Suppressors," *Trends Cell Biol.* 3(2):36–39 (Feb. 1993).

Heffetz, D., et al., "The Insulinomimetic Agents $H_2O_2$ and Vanadate Stimulate Protein Tyrosine Phosphorylation in Intact Cells," *J. Biol. Chem.* 265:2896–2902 (1990).

Herrenknecht, K., et al., "Endothelial Cadherins and the Regulation of Tight Junction Permeability," Abstract (distributed at meeting) from British Society for Immunology Spring Meeting 1994, University of Southampton, United Kingdom, Mar. 23–25, 1994.

Herrenknecht, K., et al., "Tyrosine Phosphorylation and Tight Junction Permeability. II," Abstract (distributed at meeting) from Autumn Meeting of the British Society for Cell Biology, University of Oxford, UK, Sep. 18–21, 1994.

John, V., et al., "The Effect of Cyclic AMP–dependent Protein Kinase Inhibitors on Electrical Resistance in the Cell Culture Model for the Blood–Brain Barrier," *Pharm. Pharmacol. Lett.* 3(5):190–193 (Mar. 1994).

Kanner, S.B., et al., "Tyrosine Phosphorylation of a 120–Kilodalton pp60$^{src}$ Substrate upon Epidermal Growth Factor and Platelet–Derived Growth Factor Receptor Stimulation and in Polyomavirus Middle–T–Antigen–Transformed Cells," *Mol. Cell. Biol.* 11:713–720 (1991).

Kurihara, H., et al., "Increased Tyrosine Phosphorylation Accompanies Modification of Tight Junctions Between Foot Processes of Glomerular Epithelial Cells (GEC)," *Molec. Biol. Cell* 3(*Suppl.*):218a, Abstract No. 1263 (1992).

Kurihara, H., et al., "Localization and Dinamics of Tight Junction Protein, ZO–1 in Rat Glomerular Epithelial Cells," *Cell Struct. Funct.* 17(6):493, Abstract No. 1D–1615 (1992).

Langeler, E.G., and Van Hinsbergh, V.W.M., "Norepinephrine and Iloprost Improve Barrier Function of Human Endothelial Cell Monolayers: Role of cAMP," *Am. J. Physiol.* 260:C1052–C1059 (1991).

Levenson, R.M., and Blackshear, P.J., "Insulin–stimulated Protein Tyrosine Phosphorylation in Intact Cells Evaluated by Giant Two–dimensional Gel Electrophoresis," *J. Biol. Chem.* 264:19984–19993 (1989).

Linder, M.E., and Burr, J.G., "Nonmyristoylated p60$^{v-src}$ Fails to Phosphorylate Proteins of 115–120 kDa in Chicken Embryo Fibroblasts," *Proc. Natl. Acad. Sci. USA* 85:2608–2612 (1988).

Madara, J.L., "Tight Junction Dynamics: Is Paracellular Transport Regulated?," *Cell* 53:497–498 (1988).

Martinez–Palomo, A., et al., "Experimental Modulation of Occluding Junctions in a Cultured Transporting Epithelium," *J. Cell Biol.* 87:736–745 (1980).

Matsuyoshi, N., et al., "Cadherin–Mediated Cell–Cell Adhesion Is Perturbed by v–src Tyrosine Phosphorylation in Metastatic Fibroblasts," *J. Cell Biol.* 118:703–714 (1992).

Morgan, L., et al., "Molecular Control of Blood Brain Barrier Permeability," Abstract (distributed at meeting) from 8th International Workshop on in Vitro Toxicology, Zurich, Switzerland, Sep. 20–23, 1994.

Musil, L.S., et al., "Differential Phosphorylation of the Gap Junction Protein Connexin43 in Junctional Communication–,competent and –deficient Cell Lines," *J. Cell Biol.* 111:2077–2088 (1990).

Ojakian, G.K., "Tumor Promoter–Induced Changes in the Permeability of Epithelial Cell Tight Junctions," *Cell* 23:95–103 (1981).

Rubin, L.L., et al., "A Cell Culture Model of the Blood–Brain Barrier," *J. Cell Biol.* 115:1725–1735 (1991).

Rubin, L.L., "Endothelial Cells: Adhesion and Tight Junctions," *Curr. Opin. Cell Biol.* 4:830–833 (1992).

Rubin, L.L., et al., "Tight Junctions and the Blood–Brain Barrier," Abstract (distributed at meeting) from Association pour la Recherche sur La Sclerose en Plaques (ARSEP), Paris, France, Dec. 1–2, 1993.

Rubin, L.L., et al., "Signal Transduction and the Blood–Brain Barrier," Abstract (distributed at meeting) from 17th Annual Meeting of the European Neuroscience Association, Vienna, Austria, Sep. 4–8, 1994.

Rubin, L.L., et al., "Tight Junctions and the Blood–Brain Barrier," in: *Cell Culture in Pharmaceutical Research*, Fusenig, N.E., and Graf, H., eds., Berlin: Springer–Verlag, pp. 69–77 (Oct. 1994).

Rubin, L.L., et al., "Signal Transduction in Brain Endothelial Cells," Abstract (distributed at meeting) from INSERM Meeting No. 67, *In Vitro Models for Drug Transport Across Epithelial and Endothelial Barriers*, Le Vesinet, France, Oct. 13–14, 1994.

Rutten, M.J., et al., "Electrical Resistance and Macromolecular Permeability of Brain Endothelial Monolayer Cultures," *Brain Res.* 425:301–310 (1987).

Staddon, J.M., et al., "Tyrosine Phosphatase Inhibitors Increase Tight Junctional Permeability in Strain I MDCK Cells," *Molec. Biol. Cell* 4(*Suppl.*):103a, Abstract No. 599 (Oct. 1993).

Staddon, J.M., et al., "Tyrosine Phosphorylation and Tight Junction Permeability. I," Abstract (distributed at meeting) from Autumn Meeting of the British Society for Cell Biology, University of Oxford, UK, Sep. 18–21, 1994.

Staddon, J.M., et al., "Evidence that Tyrosine Phosphorylation May Increase Tight Junction Permeability," *J. Cell Sci.* 108(2):609–619 (Feb. 1995).

Stelzner, T.J., et al., "Role of Cyclic Adenosine Monophosphate in the Induction of Endothelial Barrier Properties," *J. Cell. Physiol.* 139:157–166 (1989).

Stevenson, B.R., et al., "Phosphorylation of the Tight–junction Protein ZO–1 in Two Strains of Madin–Darby Canine Kidney Cells Which Differ in Transepithelial Resistance," *Biochem. J.* 263:597–599 (1989).

Tsukita, S., et al., "Specific Proto–Oncogenic Tyrosine Kinases of src Family Are Enriched in Cell–to–Cell Adherens Junctions Where the Level of Tyrosine Phosphorylation Is Elevated," *J. Cell Biol.* 113:867–879 (1991).

Tsukita, S., et al., "Submembranous Junctional Plaque Proteins Include Potential Tumor Suppressor Molecules," *J. Cell Biol.* 123(5):1049–1053 (Dec. 1993).

Volberg, T., et al., "The Effect of Tyrosine–Specific Protein Phosphorylation on the Assembly of Adherens–Type Junctions," *EMBO J.* 11:1733–1742 (1992).

Warren, S.L., and Nelson, W.J., "Nonmitogenic Morphoregulatory Action of pp60$^{v-src}$ on Multicellular Epithelial Structures," *Mol. Cell. Biol.* 7:1326–1337 (1987).

English–language abstract for Japanese patent document No. JP 4–13631 (Doc. Ref. No. AM1), Derwent WPI Accession No. 92–069423/09.

Rubin, L.L., and Staddon, J.M., "Regulation of Blood–Brain Barrier Permeability," Abstract (distributed at meeting) from XXXII International Union of Physiological Sciences (IUPS), Glasgow, UK, Aug. 4–6, 1993.

\* cited by examiner

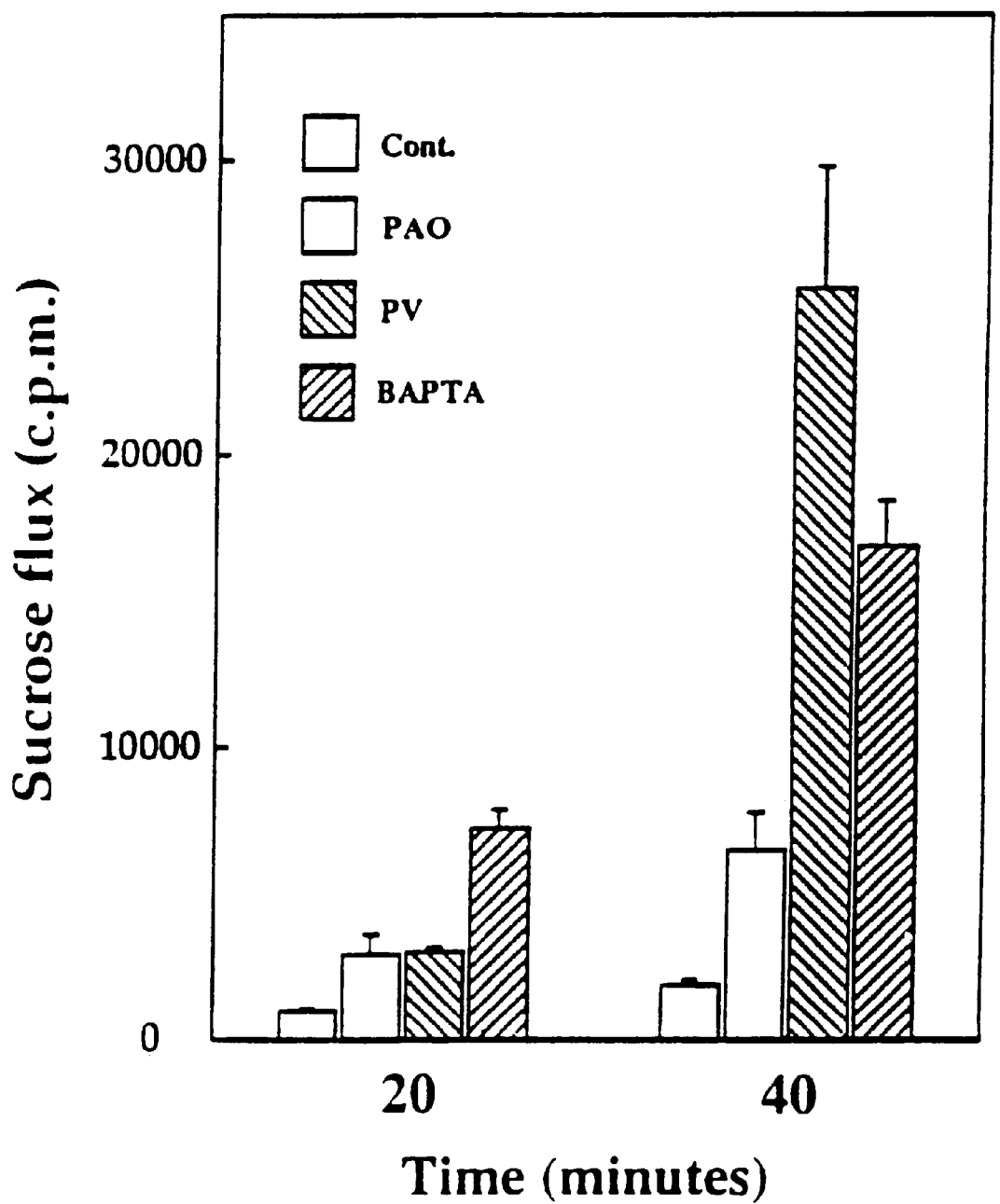
FIG. 4.1

FIG. 5.1
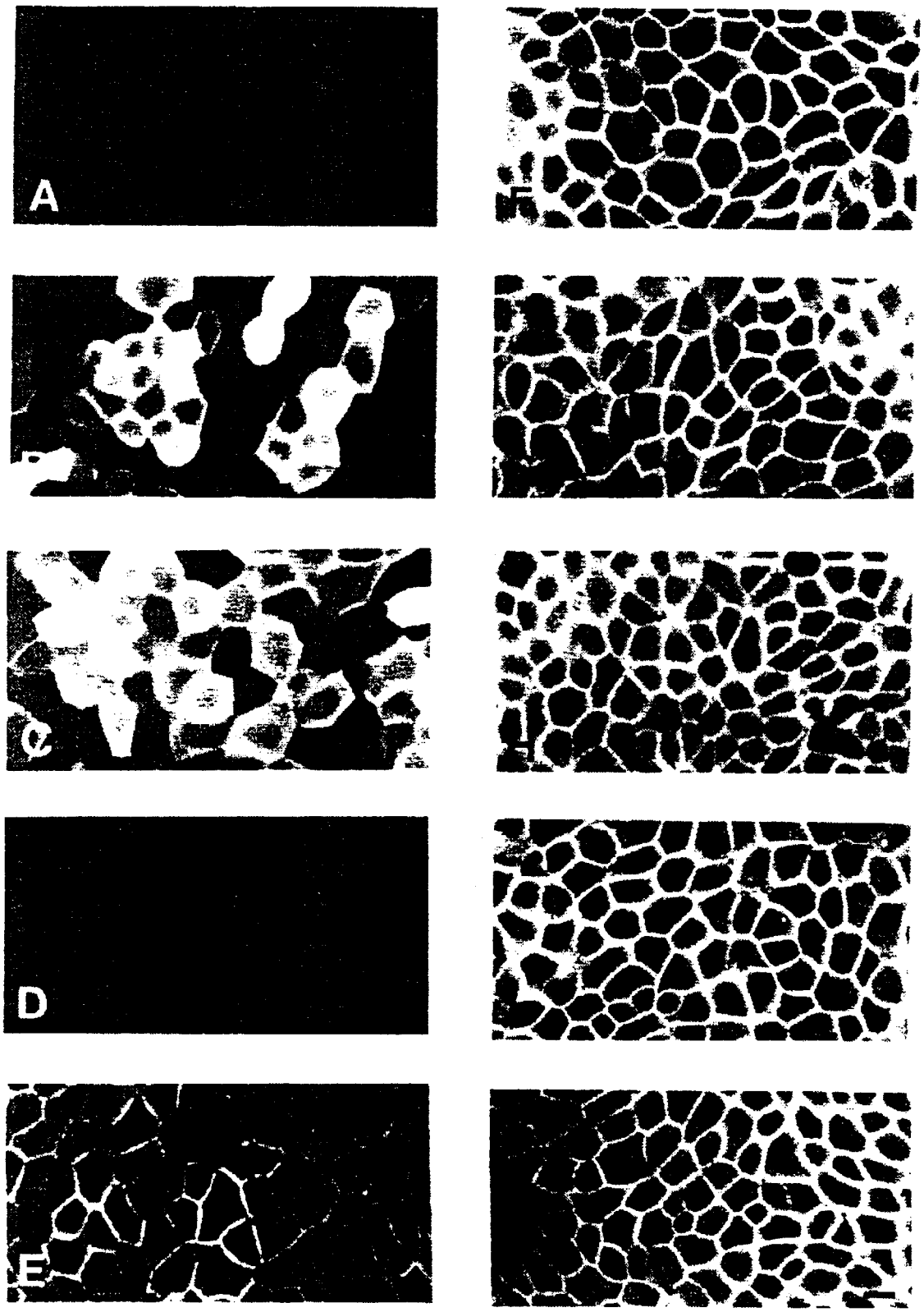

FIG. 5.2
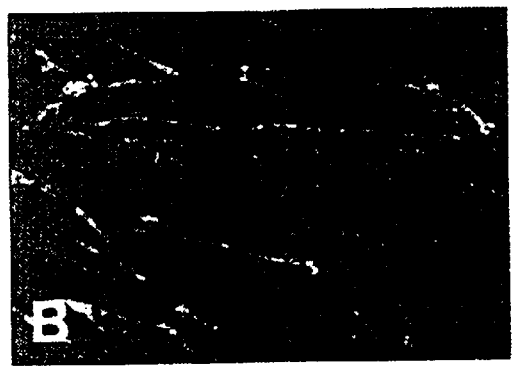
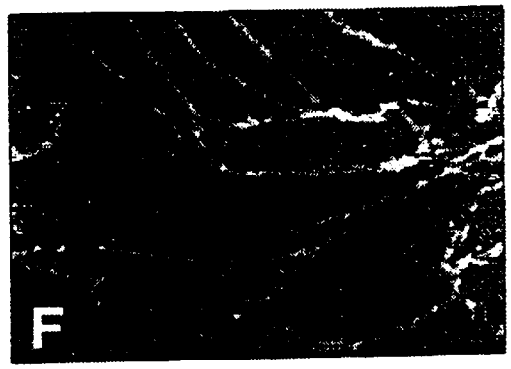

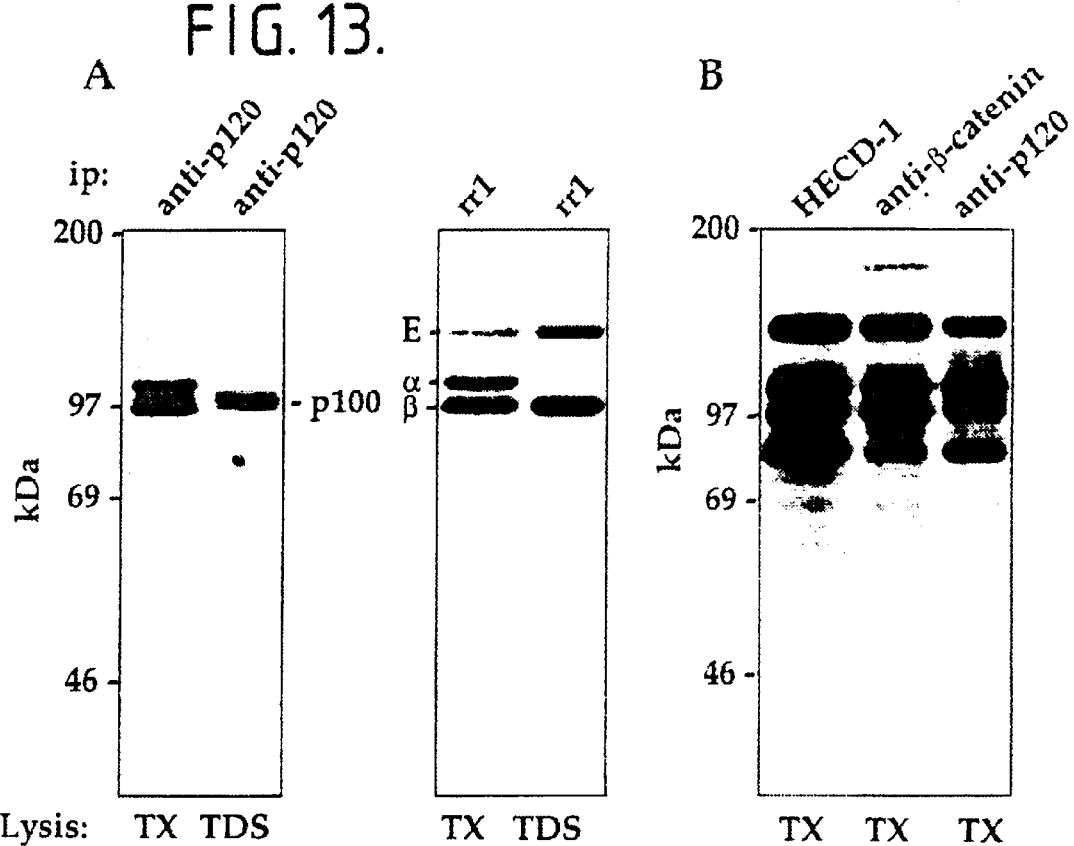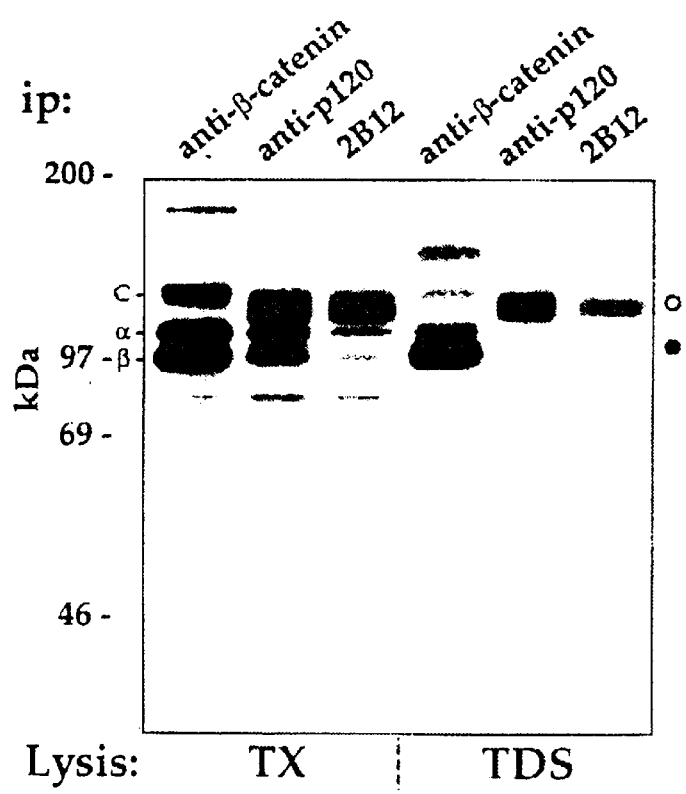

FIG. 16.
A
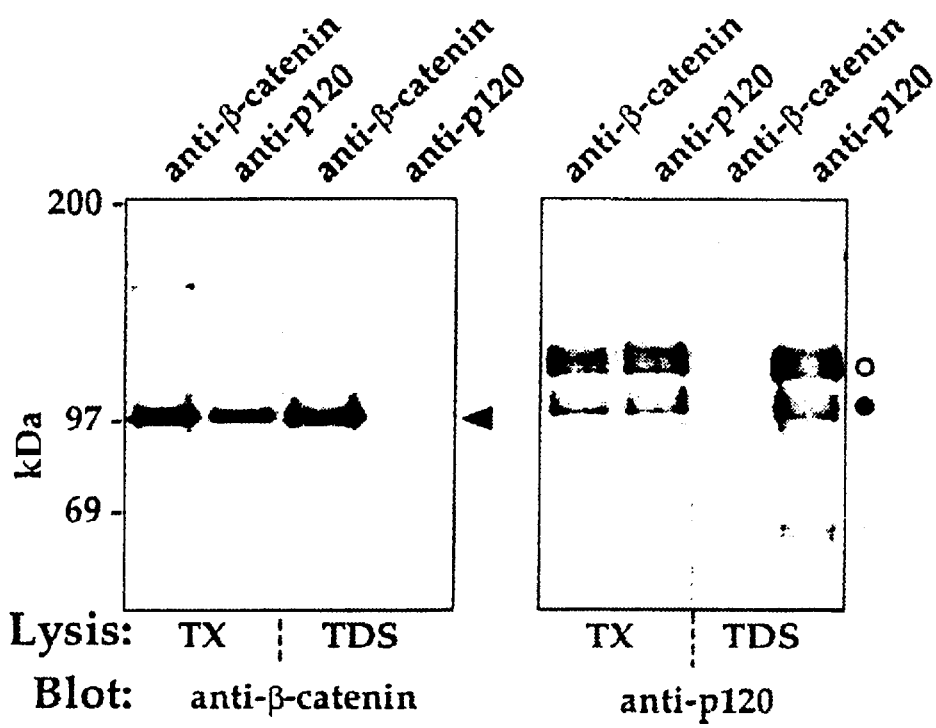
B
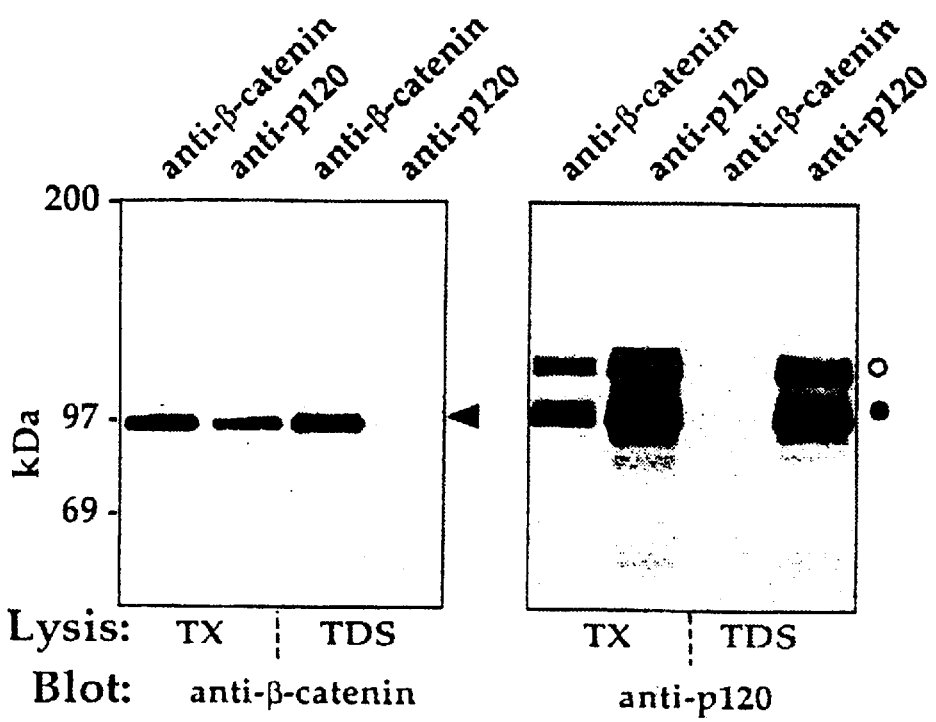

FIG. 19.

| Human p100 | | Mouse p120 | |
|---|---|---|---|
| SEQUENCER RESULTS | PUBLISHED SEQUENCE | RESIDUES |
| NISFGRDQDNK | NISFGRDQDNK | 434-444 |
| HAIPNLV | HARPNLV | 744-751 |
| XVLINK | LVLINK | 799-804 |
| XPIEDPANDTVDFPX | KPTEDPANDTVDFPX | 629-642 |
| XPSGALRNLAVDARX (Tentative) | AASGALRNLAVDARK | 723-738 |

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 11 amino acids
      (B) TYPE: amino acid
      (C) STRANDEDNESS: Not Relevant
      (D) TOPOLOGY: linear (ii) MOLECULE TYPE: peptide (xi) SEQUENCE DESCRIPTION: SEQ ID NO:1:

Asn Ile Ser Phe Gly Arg Asp Gln Asp Asn Lys
1               5                   10

(2) INFORMATION FOR SEQ ID NO:2:

(i) SEQUENCE CHARACTERISTICS:
            (A) LENGTH: 7 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:2:

His Ala Ile Pro Asn Leu Val
1               5

(2) INFORMATION FOR SEQ ID NO:3:

(i) SEQUENCE CHARACTERISTICS:
            (A) LENGTH: 6 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa at residue 1 = any
                amino acid"

(xi) SEQUENCE DESCRIPTION: SEQ ID NO:3:

Xaa Val Leu Ile Asn Lys
1               5

(2) INFORMATION FOR SEQ ID NO:4:

(i) SEQUENCE CHARACTERISTICS:
            (A) LENGTH: 15 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 1..15
            (D) OTHER INFORMATION: /note= "Xaa at residues 1 and 15 =
                any amino acid"

(xi) SEQUENCE DESCRIPTION: SEQ ID NO:4:

Xaa Pro Ile Glu Asp Pro Ala Asn Asp Thr Val Asp Phe Pro Xaa
1               5                   10                  15

(2) INFORMATION FOR SEQ ID NO:5:

(i) SEQUENCE CHARACTERISTICS:
            (A) LENGTH: 15 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 1..15

(D) OTHER INFORMATION: /note= "Xaa at residues 1 and 15 =
            any amino acid"

(xi) SEQUENCE DESCRIPTION: SEQ ID NO:5:

Xaa Pro Ser Gly Ala Leu Arg Asn Leu Ala Val Asp Ala Arg Xaa
1               5                  10                  15

(2) INFORMATION FOR SEQ ID NO:6:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:6:

His Ala Arg Pro Asn Leu Val
1               5

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:7:

Leu Val Leu Ile Asn Lys
1               5

(2) INFORMATION FOR SEQ ID NO:8:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 15
        (D) OTHER INFORMATION: /note= "Xaa at residue 15 = any
            amino acid"

(xi) SEQUENCE DESCRIPTION: SEQ ID NO:8:

Lys Pro Thr Glu Asp Pro Ala Asn Asp Thr Val Asp Phe Pro Xaa
1               5                  10                  15

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:9:

Ala Ala Ser Gly Ala Leu Arg Asn Leu Ala Val Asp Ala Arg Lys
1               5                  10                  15

MODULATING THE PERMEABILITY OF A PHYSIOLOGICAL BARRIER WITH AN AGENT THAT MODULATES TYROSINE PHOSPHORYLATION

FIELD OF INVENTION

This invention relates to the control of permeability of the blood-brain barrier and other physiological barriers.

BACKGROUND OF INVENTION

The blood-brain barrier serves to separate the molecular, ionic and cellular environment of the blood from that of the brain. To a major degree, this separation is achieved by inter-endothelial tight junctions of high electrical resistance which greatly diminish paracellular flux. It is clear that the permeability of the tight junctions of the blood-brain barrier is not immutable. Rather, permeability appears to undergo dynamic regulation, especially by second messenger pathways.

Acquiring the ability to manipulate the permeability of the tight junctions of the blood-brain barrier is important for a number of reasons, among which are the following:

(i) To decrease brain oedema following stroke by closing the tight junctions of the blood-brain barrier;

(ii) To deliver blood-borne, membrane-impermeant drugs to the brain by reversibly opening the tight junctions of the blood-brain barrier; and (iii) To block the entry into the brain of both leukocytes that mediate an immune response, such as occurs in multiple sclerosis, and metastatic cancer cells that may form tumours. (It is believed that during cell trafficking across the endothelium, the migrating cell passes through the tight junction must therefore trigger intra-endothelial mechanisms that influence junctional permeability.)

It is also desirable to manipulate the permeability of other physiological barriers involving tight junctions.

At the molecular level, some of the components of the tight junction complex have been identified. These include ZO-1 (Stevenson et al., 1986; Willot et al., 1993), $\alpha^+$ and $\alpha^-$ isoforms (Willot et al., Balda and Anderson, 1993), ZO-2 (Gumbiner et al., 1991), cingulin (Citi et al., 1988) and the 7H6 antigen (Zhong et al., 1993), all of which are associated with the cytoplasmic surface of the tight junction in a manner yet to be fully determined. Also, a 130 kDa phosphorprotein that appears to associate with ZO-1 and ZO-2 in an unspecified manner has recently been described (Balda et al., 1993). Finally, an integral membrane protein, termed occludin, that localizes at tight junctions has also been identified (Furuse et al., 1993).

It is clear that in endothelia and certain epithelia, the ability of tight junctions to restrict paracellular flux is not immutable. Rather, this gate function of tight junctions is capable of dynamic regulation (Madara, 1988; Rubin, 1992). In particular, the activation of signal transduction pathways either by receptor ligands or specific membrane-permeant modulators can have striking effects on the permeability of the paracellular pathway. For example, protein kinase C activation causes a substantial increase in the permeability of tight junctions in MDCK cells (Ojakian, 1981), an epithelial cell line. Cyclic AMP elevation decreases permeability in brain endothelial cells in culture, a model system for the study of the blood-brain barrier (Rubin et al., 1991). Cyclic AMP also decreases tight junction permeability in peripheral endothelial cells (Stelzner et al., 1989; Langeier et al., 1991).

The permeability properties of the tight junction also depend upon the integrity of the adherens junction. Disruption of the adherens junction by removal of extracellular $Ca^{2+}$ leads to an opening of tight junctions in MDCK cells (see Martinez-Palomo et al., 1980; Gumbiner and Simons, 1986) and in endothelial cells (Rutten et al., 1987). Protein kinases appear to be involved in this indirect modulation of tight junctional integrity in MDCK cells (Citi, 1992). The $Ca^{2+}$-sensitive components of the adherens junction complex are the cadherins (reviewed by Geiger and Avalon, 1992). These transmembrane proteins mediate intercellular adhesiveness in a $Ca^{2+}$-dependent, homophilic manner via their extracellular domains. The cytoplasmic domain of the cadherins associates with three further proteins termed $\alpha$-, $\beta$- and $\gamma$-catenin (Ozawa et al., 1989), which link the cadherins to the actin cytoskeleton and are required for cadherin adhesiveness (Hirano et al., 1987; Nagaruchi and Takeichi, 1988; Ozawa et al., 1990; Kintner, 1992; see Stappert and Kemler, 1993).

Recently, it was reported that treatment of cells with pervanadate, a tyrosine phosphatase inhibitor, or overexpression of the tyrosine kinase $pp60^{v-src}$, resulted in the tyrosine phosphorylation of components of the cadherin/catenin complex (Matsuyoshi et al., 1992; Behrens et al., 1993; Hamaguchi et al., 1993). Such increased phosphorylation with associated with decreased cadherin-dependent cell adhesiveness (Matsuyoshi et al., 1992; Behrens et al., 1993; Hamaguchi et al., 1993). With respect to tight junctions, the relationship between protein tyrosine phosphorylation and structure has been studied, but, so far, with negative results. Warren and Nelson (1987) found that transfection of MDCK cells with low-levels of $pp60^{v-src}$ caused disruption of the adherens junction but, as revealed by electron microscopy, apparently did not affect the tight junction. Volberg et al. (1992) showed that pervanadate elicited tyrosine phosphorylation of proteins at the adherens junction in MDCK cells, but, in contrast to the findings of the present inventors, also had no effect on the tight junction, as determined by immunocytochemical examination of ZO-1 distribution.

Experiments were also carried out to investigate the effect of tyrosine phosphorylation on tight junctional permeability using bovine brain microvessel endothelial cells (BBECs) as a tissue culture model of the blood brain barrier (Rubin et al, *J. Cell Biol.* 115 1725–1735 (1991)). Since it is clear that the permeability of the tight junctions of epithelial cells is also subject to regulation, studies leading up to the present invention also used Madin-Darby canine kidney (MDCK) strain I cells, an epithelial cell line that possesses tight junctions of high intrinsic electrical resistance (several thousand $\Omega\text{-cm}^2$). In both cases, the cells were grown on filters so that the permeability of the tight junctions could be determined by measuring transcellular electrical resistance (TER). When cells are grown in this manner, the movement of molecules and cells across the monolayer can also be studied.

Other investigators have examined the relationship between protein tyrosine phosphorylation and tight junctional permeability, but with negative results. Warren and Nelson *Mol. Cell. Biol.* 7 1326–1337 (1987) found that transfection of MDCK cells with low-levels of the tyrosine kinase $pp60^{v-src}$ caused disruption of the adherens junction but apparently did not affect the tight junction, as revealed by electron microscopy. Using MDCK cells, Volberg et al, *EMBO J.* 11 1733–1742 (1992) showed that pervanadate, a tyrosine phosphatase inhibitor, elicited tyrosine phosphorylation of proteins at the adherens junction, but had no effect on the tight junction as determined by immunostaining of the tight junction associated protein, ZO-1 (see review on tight junction by S. Citi, *J. Cell Biol.* 121 485–489 (1993)).

SUMMARY OF INVENTION

The present invention is based, in contrast, on the surprising discovery that tyrosine protein phosphorylation is crucial to the control of the permeability of tight junctions in both epithelial and endothelial cells; tyrosine protein phosphorylation may therefore be manipulated to control the permeability of the blood-brain and other physiological barriers. Decreasing the degree of tyrosine protein phosphorylation reduces permeability of the blood-brain or other barrier, whereas increasing the degree of tyrosine protein phosphorylation increases permeability.

According to a first aspect of the invention, there is provided the use of an agent which promotes tyrosine protein dephosphorylation in the preparation of a medicament for reducing permeability of a physiological barrier such as the blood-brain barrier. The invention therefore has use in a method of reducing permeability of a physiological barrier such as the blood-brain barrier, the method comprising administering to a subject an effective amount of an agent which promotes tyrosine protein dephosphorylation.

According to a second aspect of the invention, there is provided the use of an agent which promotes tyrosine protein phosphorylation in the preparation of a medicament for increasing permeability of a physiological barrier such as the blood-brain barrier. The invention therefore also has use in a method of increasing permeability of a physiological barrier such as the blood-brain barrier, the method comprising administering to a subject an effective amount of an agent which promotes tyrosine protein phosphorylation.

In vivo tyrosine phosphatases cause dephosphorylation of appropriate proteins at tyrosine residues and tyrosine kinases cause corresponding phosphorylation. Compounds which directly or indirectly activate tyrosine protein phosphatase and/or which directly or indirectly inhibit tyrosine kinase are therefore useful as promoters of tyrosine protein dephosphorylation and consequently as agents for reducing permeability of physiological barriers such as the blood-brain barrier. Conversely, compounds which directly or indirectly inhibit tyrosine protein phosphatase and/or which directly or indirectly activate tyrosine kinase are useful as promoters of tyrosine protein phosphorylation and consequently as agents for increasing permeability of physiological barriers such as the blood-brain barrier. In all cases, it will be preferred for the effects to be reversible or sufficiently reversible to avoid untoward toxicity problems. Preferred embodiments of the invention will now be described with reference to the accompanying drawings, in which:

BRIEF DESCRIPTION OF THE DRAWINGS

FIGS. 4a, 4b, 4c and 4d show graphically that pervanadate and phenylarsine oxide decrease the transcellular electrical resistance (and by implication increase permeability) of brain capillary endothelial cells;

FIGS. 5a, 5b, 5c and 5d are luminograms showing that pervanadate increases the tyrosine phosphorylation of many proteins in MDCK strain I cells and BBECs, in comparison to the discrete effects of phenylarsine oxide.

FIG. 5.2 shows that PAO increases the tyrosine phosphorylation of proteins at intercellular junctions in brain endothelial cells and also shows a comparison with the effect of pervanadate.

FIG. 13 shows a comparison of anti-p120 and anti-E-cadherin immunoprecipitates from MDCK and Caco-2 cells.

FIG. 15 shows a comparison of anti-β-catenin, anti-p120 and 2B12 immunoprecipitates from primary cultures of bovine brain endothelial cells.

FIG. 16 shows the detection of p120/p100 in β-catenin immunuoprecipitates and β-catenin in anti-p120 immunoprecipitates from human umbilical vein endothelial cells (Panel A) and ECV304 cells (Panel B).

FIG. 19 shows a comparison of partial amino acid sequence data obtained for human p100 (SEQ ID NOs:1–5) with corresponding known sequence data from mouse p120 (SEQ ID NOs:6–9). The letters given are based on the standard single letter amino acid code, apart from "X", which indicates any amino acid.

DETAILED DESCRIPTION OF THE INVENTION

Figure 1:
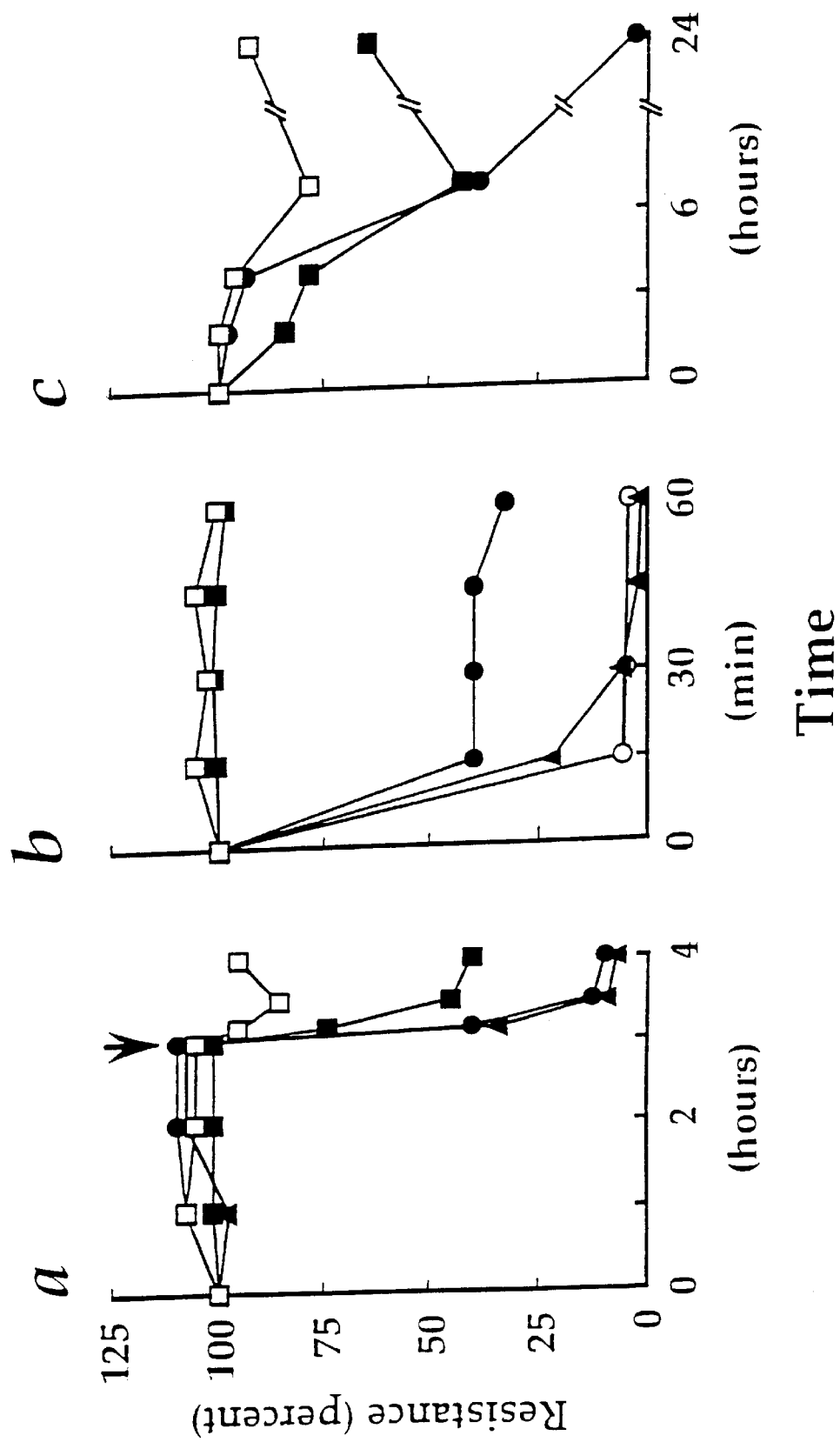
FIGS. 1a, 1b and 1c show graphically that pervanadate decreases the transcellular electrical resistance (and by implication increases permeability) of strain I MDCK cells.

In initial experiments, cells were treated with vanadate, a non-selective, but potent, inhibitor of tyrosine phosphatases. In MDCK cells, vanadate alone did not cause a decrease in TER. However, the addition of $H_2O_2$ to vanadate pretreated cells caused a rapid decrease in TER (FIG. 1a), indicative of an increased permeability of the tight junctions. Vanadate is relatively membrane-impermeant, but $H_2O_2$ oxidises vanadate to membrane-permeant pervanadate which then enters the cells to inhibit tyrosine phosphatases (see eg Fantus et al, *Biochemistry* 28 8864–8871 (1989); Volberg et al, *Cell Regulation* 2 105–120 (1991); O'Shea et al, *Proc. Natl. Acad. Sci. U.S.A.* 89 10306–10310 (1992)). Indeed, preformed pervanadate elicited a decrease in TER (FIG. 1b). Over a longer time period, vanadate alone caused a decrease in TER (FIG. 1c), presumably because of its eventual entry into the cells.

Figure 2:
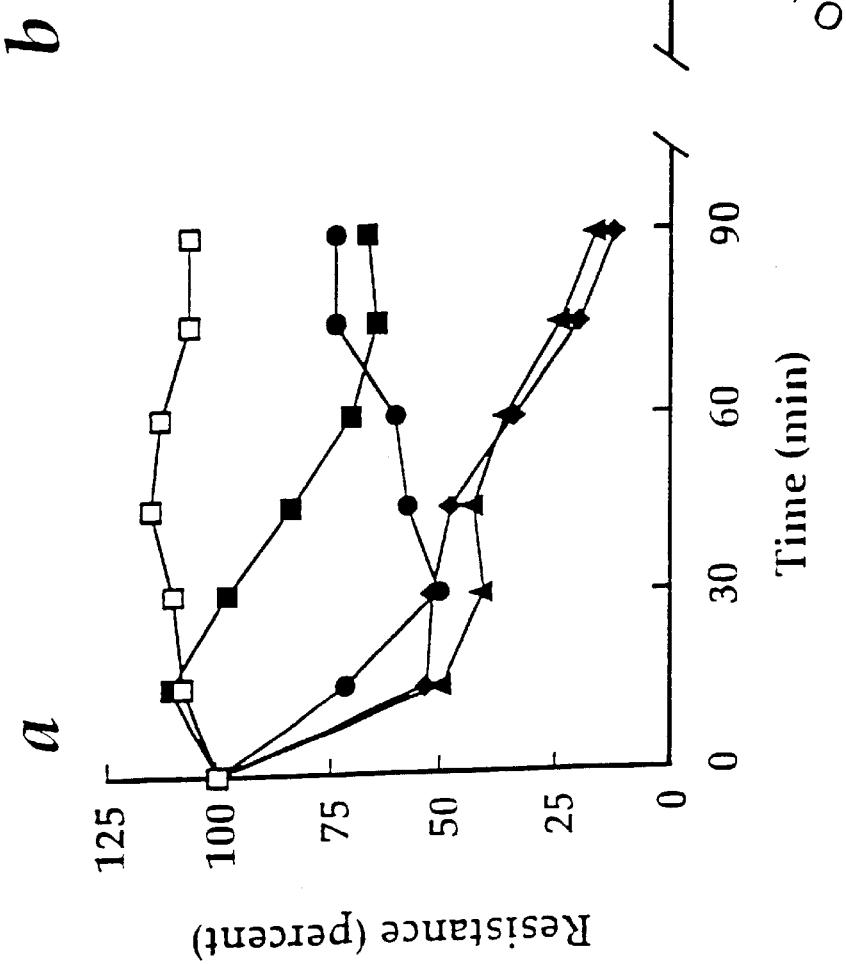
FIGS. 2a and 2b show graphically that phenylarsine oxide decreases the transcellular electrical resistance (and by implication increases permeability) of MDCK I cells.

A more selective inhibitor of tyrosine phosphatases is phenylarsine oxide (PAO). It inhibits by covalently reacting with closely spaced sulphydryl groups of the phosphatase (see Levenson and Blackshear, *J. Biol. Chem.* 264 19984–19993 (1989); Garcia-Morales et al, *proc. natl. Acad. Sci. U.S.A.* 87 9225:9259 (1990); Pronk et al, *J. Biol. Chem.* 267 24058–24063 (1992)). It was found that PAO could also cause a decrease in TER of MDCK strain I cells (FIG. 2a). PAO action was blocked by the dithiol, 2,3-dimercaptopropanol, but not by β-mercaptoethanol (FIG. 2b), as expected for PAO mediated inhibition via the appropriate configuration of sulphydryls. Dimercaptopropanol did not block the decrease in TER elicited by the $Ca^{2+}$ chelator bis-(O-aminophenoxy)-ethane-N,N,N',N'-tetraacetic acid (BAPTA), indicating selectivity in the inhibition of PAO action (FIG. 2b). Both reducing agents, however, blocked the action of pervanadate (FIG. 2b), probably by simple reduction of pervanadate to vanadate.

The decrease in TER induced by pervanadate (FIG. 3a) or PAO (FIG. 3b) could be partially reversed or completely reversed, respectively, by reducing agent if added early enough. Thus, tyrosine phosphatase inhibitors elicit a reversible opening of tight junctions in MDCK strain I cells.

Figure 4:
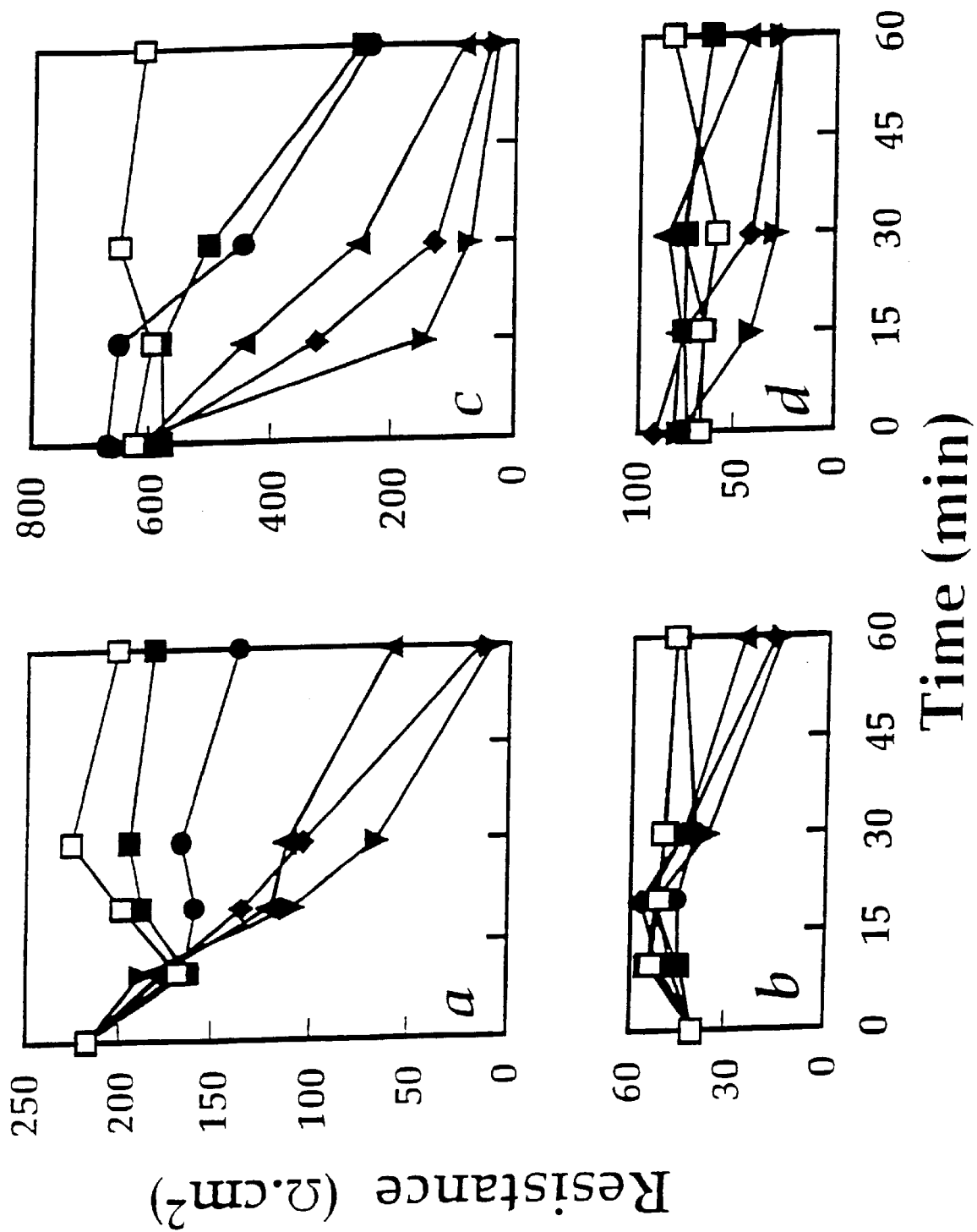
FIG. 4.1 shows that PAO and pervanadate increase the paracellular flux of sucrose in MDCK cells.

In the BBECs, pervanadate and PAO similarly caused a dose-dependent and rapid decrease in TER (FIGS. 4a to 4d). It was previously shown that cyclic AMP increases TER, ie decreases leakiness of tight junctions, in the BBECs as well as in endothelial cells derived from human brain (Rubin et al, *J. Cell Biol.* 115 1725–1735 (1991)). The pervanadate- and PAO-induced decrease in TER was observed in BBECs treated with or without cyclic AMP (FIGS. 4a,c with FIGS. 4b,d).

In normal cells, the degree of tyrosine phosphorylation of proteins reflects the balance of the activities of tyrosine kinases and tyrosine phosphatases. Pervanadate and PAO, by inhibition of tyrosine phosphatases, must cause increased protein tyrosine phosphorylation through active kinases. To investigate the mechanism whereby the phosphatase inhibitors decrease TER, the subcellular localisation of tyrosine phosphorylated proteins was first determined. This was achieved by immunostaining using an anti-phosphotyrosine antibody (PY20) (ICN Biomedicals, Ltd). In this procedure, the cells are fixed in paraformaldehyde to preserve the organisation and covalent modifications of proteins as found in the intact cell. After membrane-permeabilisation, the fixed cells are incubated with antibody and sites of bound antibody are detected using a flurochrome-conjugated secondary antibody followed by fluorescence microscopy.

In both the MDCK cells and BBECs, 100 μM pervanadate initially caused an increase in staining at the adherens junction at the intercellular borders. This pattern of staining is similar to that previously reported (see Volberg et al, *Cell Regulation* 2 105–120 (1991); Volberg et al, *EMBO J.* 11 1733–1742 (1992)). In contrast, PAO (10 μM) caused only an increase in border staining of the MDCK strain I cells at times of decreased TER. In the BBECs, PAO (10 μM) caused a transient increase in border staining of the cells. These observations indicate that substrates for tyrosine kinases must be present at intercellular junctions. However, these studies give no information as to the identity of the tyrosine phosphorylated proteins.

Figure 5:
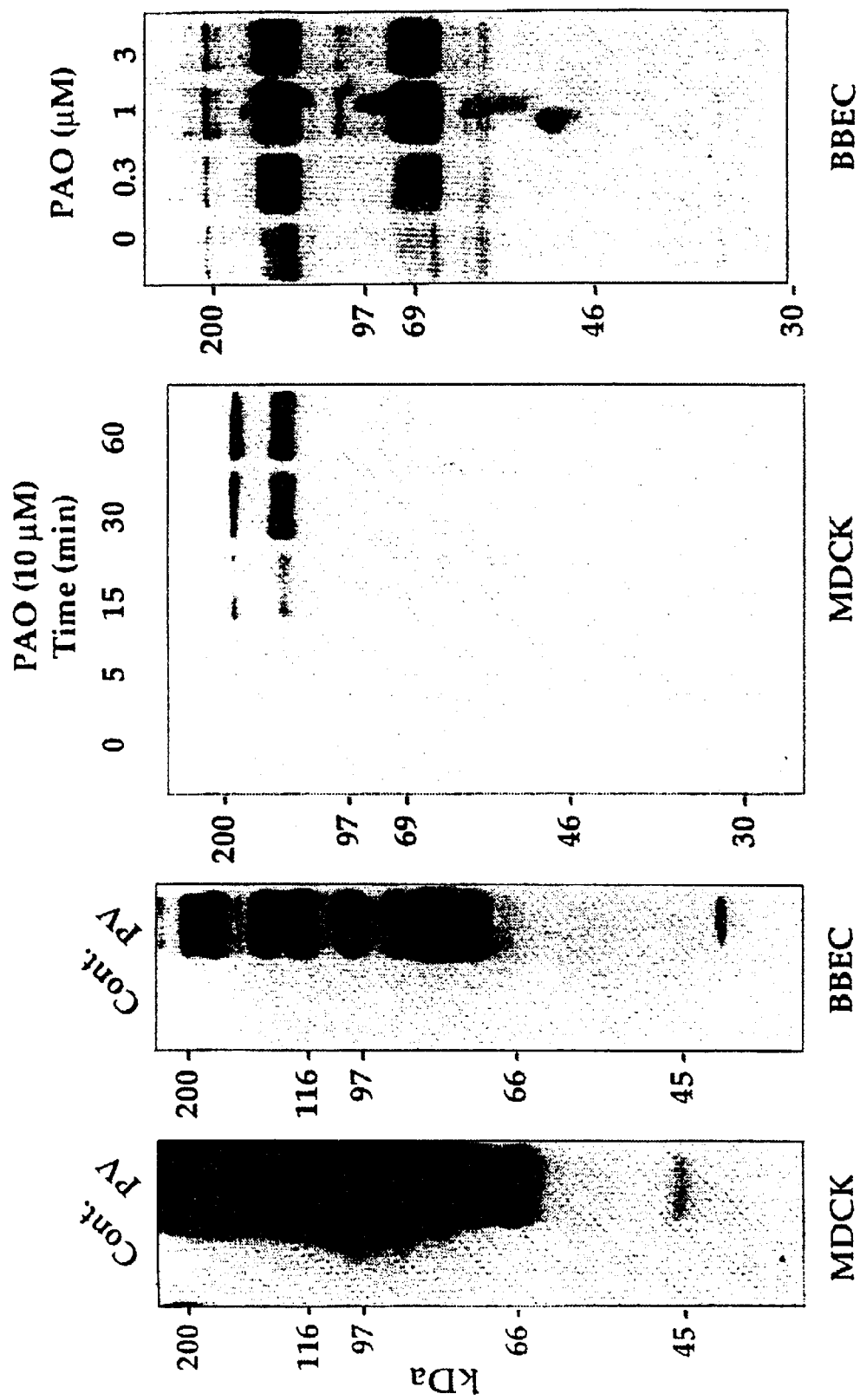
FIG. 5.1 shows that PAO increases the tyrosine phosphorylation of proteins at intracellular junctions in MDCK cells and also shows a comparison with the effect of pervanadate.

The tyrosine phosphorylation of individual proteins was examined by immunoblotting using an anti-phosphotyrosine antibody. Initially, phosphorylation of proteins in whole cell lysates was examined to gauge the selectivity of action of the phosphatase inhibitors. Pervanadate caused an increase in the tyrosine phosphorylation of many proteins in both the MDCK cells (FIG. 5a) and the BBECs (FIG. 5b). In contrast, concentrations of PAO that caused a decrease in TER had much more of a discrete effect, eliciting the phosphorylation of only a few proteins in both the MDCK cells (FIG. 5c) and BBECs (FIG. 5d).

To determine the identity of proteins that control tight junction permeability, it is necessary to known that tight junctional permeability is known to be influenced by the integrity of the adherens junction. Removal of extracellular $Ca^{2+}$ leads to an increase in the permeability of the tight junction presumably by disruption of the adherens junction (see Gumbiner et al, *J. Cell. Biol.* 107 1575–1587 (1988)). The $Ca^{2+}$-sensitive components of the junctional complex are the cadherins. These transmembrane proteins mediate intercellular adhesiveness in a $Ca^{2+}$-dependent, homophilic manner via their extracellular domain. The cytoplasmic domain of the cadherins associates with three further proteins termed α-, β- and γ-catenins, which link the cadherins to the cytoskeleton (Stappert and Kemler, *Curr. Opinion in Neurobiol.* 3 60–66 (1993)). Recently, it was reported that pervanadate treatment or $pp60^{v-src}$ over-expression resulted in the tyrosine phosphorylation of components of the cadherin/catenin complex (Matsuyoshi et al, *J. Cell Biol.* 118 703–714 (1992); Behrens et al, *J. Cell Biol.* 120 757–766 (1993); Hamaguchi et al, *EMBO J.* 12 307–314 (1993)). Such increased phosphorylation was associated with decreased cadherin-dependent cell adhesiveness (Matsuyoshi et al, *J. Cell Biol.* 118 703–714 (1992); Behrens et al, *J. Cell Biol.* 120 757–766 (1993); Hamaguchi et al, *EMBO J.* 12 307–314 (1993)).

It is possible that pervanadate and PAO increase the permeability of tight junctions by causing the tyrosine phosphorylation of components of the cadherin/catenin complex. It was therefore decided to examine more closely the effect of pervanadate and PAO on the tyrosine phosphorylation of this complex in MDCK strain I cells. The complex was immunoprecipitated from cells solubilised in a way that preserves pre-existing protein interactions using rrl, a mouse monoclonal antibody that recognises E-cadherin (Gumbiner et al, *J. Cell Biol.* 102 457–468 (1986)). Immunoprecipitated proteins were separated by SDS-PAGE, and tyrosine phosphorylation was detected by immunoblotting using an anti-phosphotyrosine antibody and enhanced chemiluminescence.

1. Catenin Tyrosine Kinase substrates (i) β-catenin, not α-, appears to be phosphorylated in response to PAO Pervanadate caused an increase in the tyrosine phosphorylation of several proteins in anti-E-cadherin immunoprecipitates with molecular means expected of E-cadherin (120 kDa) and associated catenins (molecular mass range, –80–102 kDa: FIG. 6A). However, PAO predominantly stimulated the tyrosine phosphorylation of only one of the catenins (FIG. 6A), which on the basis of apparent molecular mass could be α- or β-catenin.

To address the issue of the identity of the catenin phosphorylated in response to PAO, peptide-directed antibodies were raised that specifically recognize α- or β-catenin. PAO-treated cells were lysed in SDS, followed by heating to dissociate protein complexes. Under these conditions only individual tyrosine phosphorylated proteins, not proteins associated with tyrosine phosphoproteins, are immunoprecipitated using anti-phosphotyrosine antibody. In such immunoprecipitates, β-catenin is rapidly increased in response to treatment of the cells with either PAO or, as expected, pervanadate (FIG. 6B). However, α-catenin was not detectable in the phosphotyrosine immunoprecipitates (FIG. 6C). Moreover, PAO- or even pervanadate-stimulated tyrosine phosphorylation of α-catenin could not be detected (FIG. 6E) in α-catenin immunoprecipitates (FIG. 6D). Thus, the tyrosine phosphorylation of β-catenin phosphorylation is increased in response to PAO, accounting for its immunoprecipitation by phosphotyrosine antibody. Furthermore, this increased phosphorylation appears to be rather selective in that α-catenin does not appear to be tyrosine phosphorylated.

(ii) Reversibility of catenin phosphorylation

Figure 3:
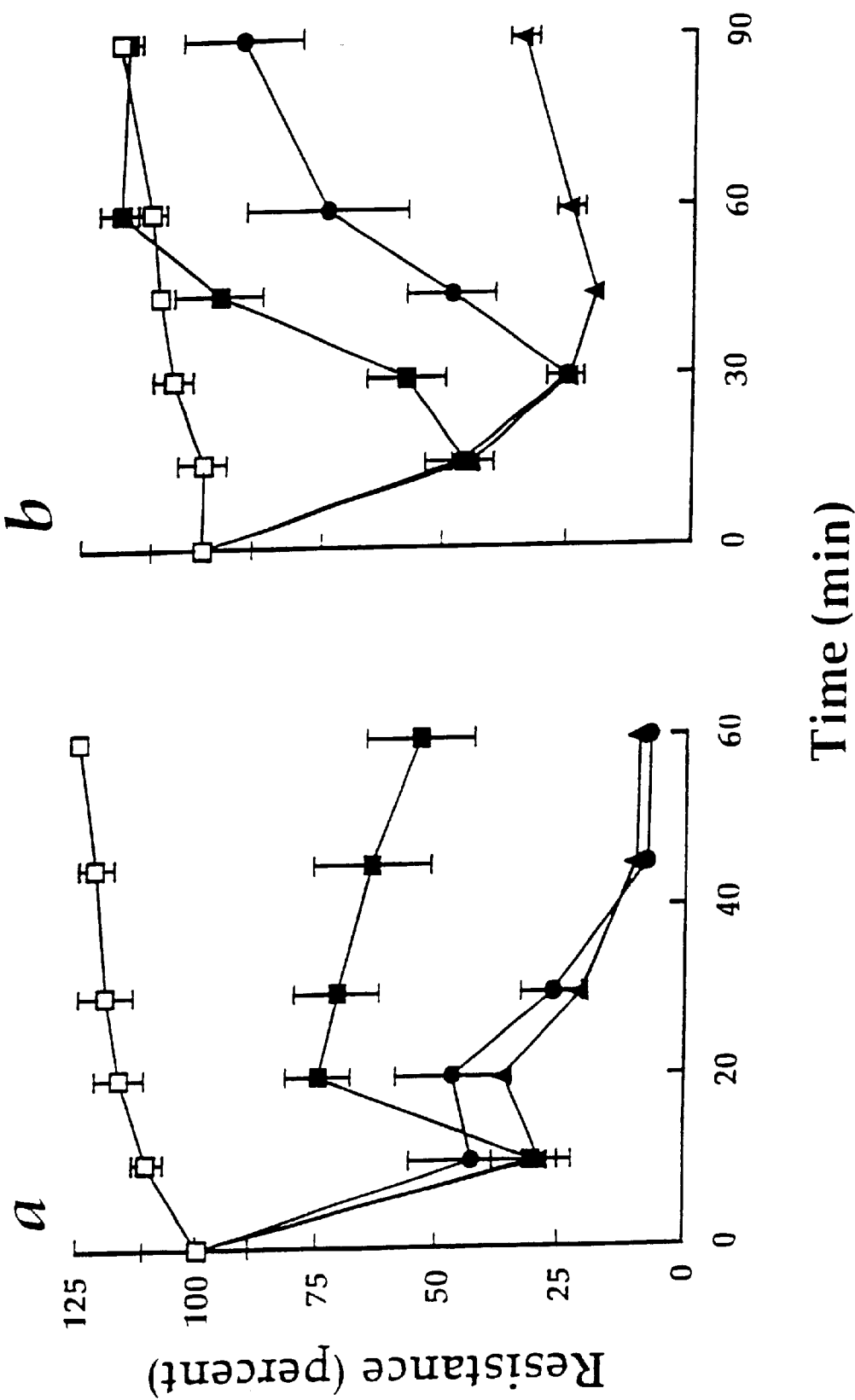
FIGS. 3a and 3b graphically the reversibility of the decrease in transcellular electrical resistance induced by tyrosine phosphatase inhibitors.

Since the effects of PAO on TER could be reversed by reducing agents, it was determined whether catenin phosphorylation was similarly reversed. Cells were treated for 15 minutes with PAO to stimulate tyrosine phosphorylation of the catenin, and then treated with or without 2,3-dimercaptopropanol for a further 45 minutes, (FIG. 3). The tyrosine phosphorylation of the catenin observed at 15 minutes persisted for up to 60 minutes (FIG. 6F). However, addition of 2,3-dimercaptopropanol reversed catenin tyrosine phosphorylation as content of the immunoprecipitates was relatively invariable (FIG. 6G), indicating quantitatively successful immunoprecipitation of the complex under all conditions. Thus, the reversible decrease in TER induced by PAO correlated with reversible catenin tyrosine phosphorylation.

(iii) Tight junction-associated proteins are tyrosine phosphorylated

Figure 7:
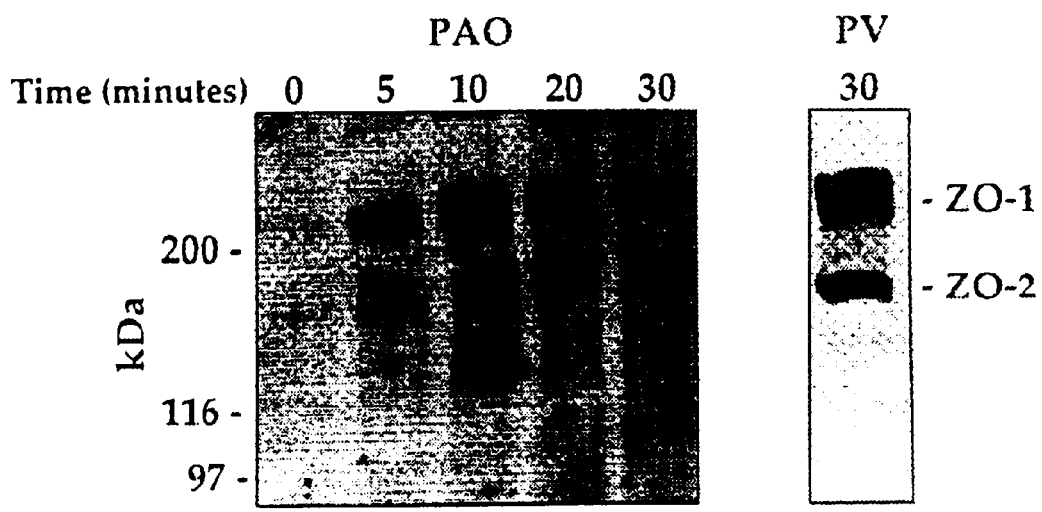
FIG. 7 shows that PAO stimulates the tyrosine phosphorylation of tight junction associated proteins in MDCK cells.

Although tight junction permeability is known to be dependent on the adherens junction, and it is shown using PAO that catenin phosphorylation correlates with the decrease in TER, it is possible that tight junction-associated proteins may also be substrates for tyrosine kinases. Therefore, the possibility that tight junction associated proteins in MDCK cells were tyrosine phosphorylated in response to PAO was examined. ZO-1 and its associated protein ZO-2 were immunoprecipitated using an anti-ZO-1 antibody and tyrosine phosphorylation was examined by immunoblotting. PAO clearly stimulated the tyrosine phosphorylation of ZO-1 and to a lesser extent that of ZO-2 (FIG. 7). Pervanadate clearly resulted in the tyrosine phosphorylation of ZO-1, ZO-2 and, to a much lesser extent, that of a protein of 130 kDa (FIG. 7), possibly the same protein as that identified by Balda, M. S., Gonzalez-Mariscal, L., Matter, K., Cereijido, M. and Anderson, J. M., 1993, Assembly of the tight junction;the role of diacylglycerol. *J. Cell Biol.* 123: 293–302. These data illustrate that tight junction proteins as well as catenins are phosphorylated in response to PAO, raising the possibility that modulation of tight junction permeability could be achieved, either directly or indirectly, via changes in adherens junction adhesiveness and/or by direct modulation of tight junction permeability.

Further data is provided later on which shows that certain proteins which are associated with the cadherin/catenin complex can also be tyrosine phosphorylated.

2. The tyrosine kinase inhibitor herbimycin A attenuates the effects of PAO (i) Tight junction permeability Pretreatment of MDCK cells with herbimycin A attenuated the decrease in transcellular electrical resistance elicited by subsequent addition of PAO (FIG. 8).

(ii) Protein tyrosine phosphorylation

Figure 9:
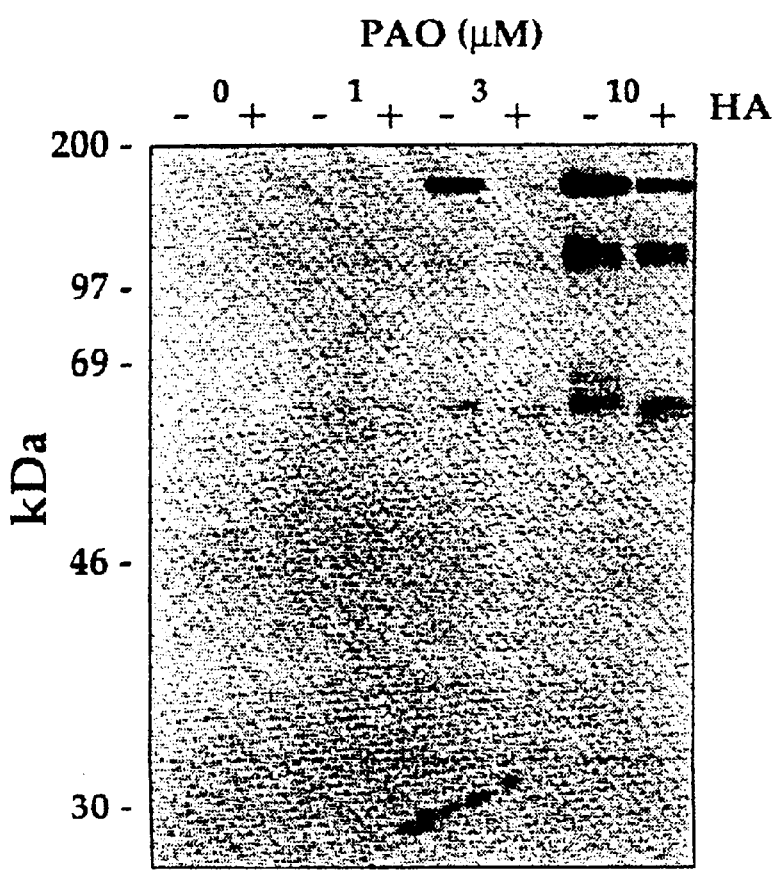
FIG. 9 shows that Herbimycin A attenuates the PAO-induced increase in protein tyrosine phosphorylation in MDCK cells.
Figure 8:
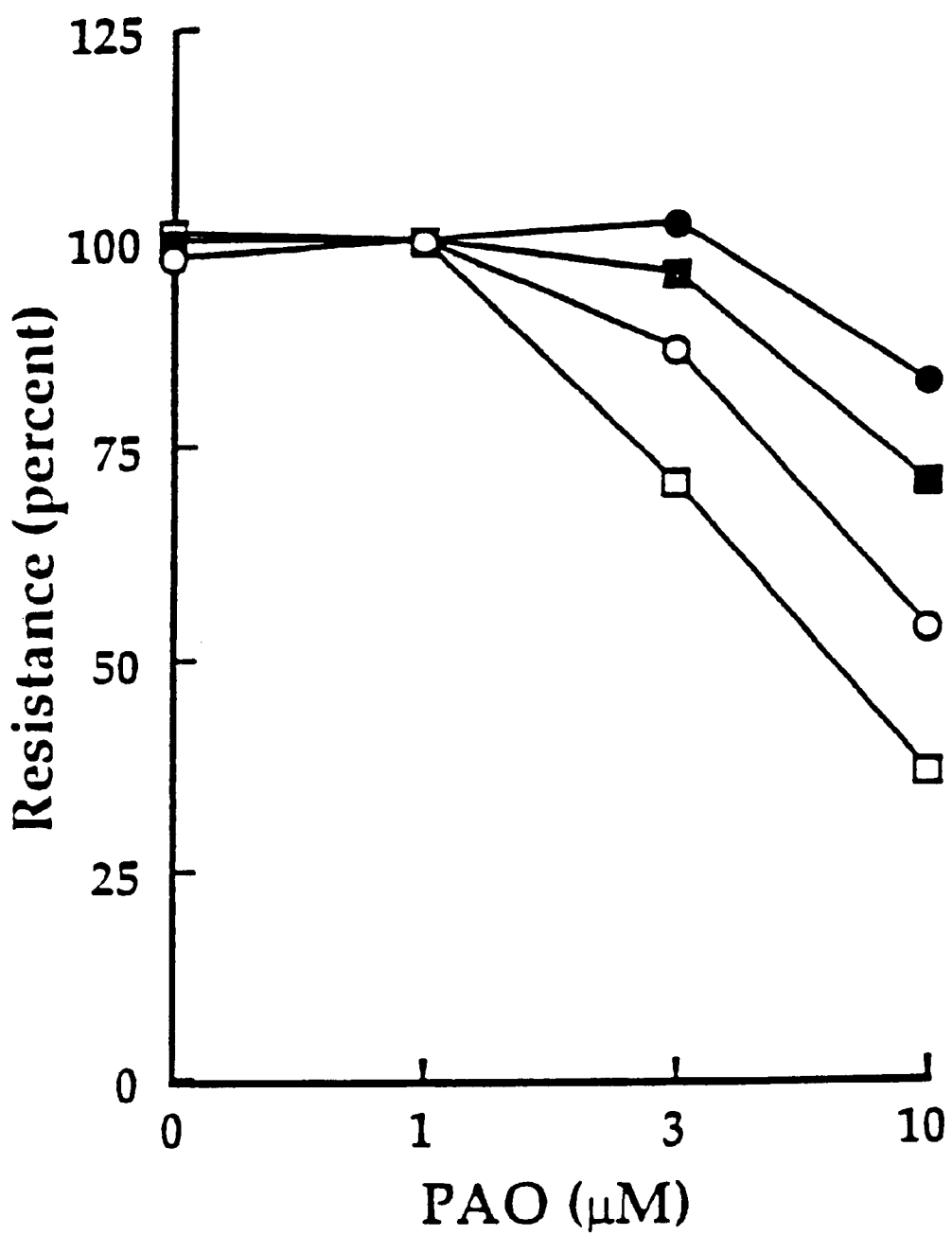
FIG. 8 shows that Herbimycin A attenuates the PAO-induced decrease in transcellular electrical resistance in MDCK cells.
Figure 10A:
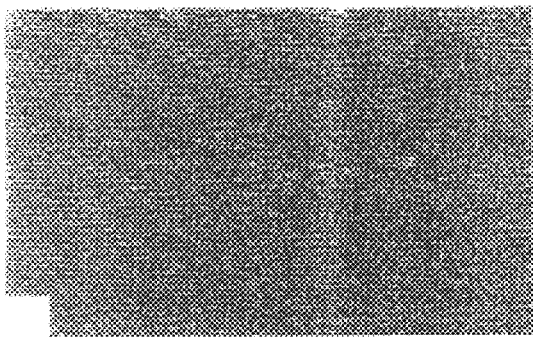
FIG. 10 shows that middle cerebral artery occlusion (a stroke model) elevates the levels of tyrosine phosphorylation in brain capillary endothelial cells associated with small blood vessels near the area damaged by the occlusion.
Figure 10B:
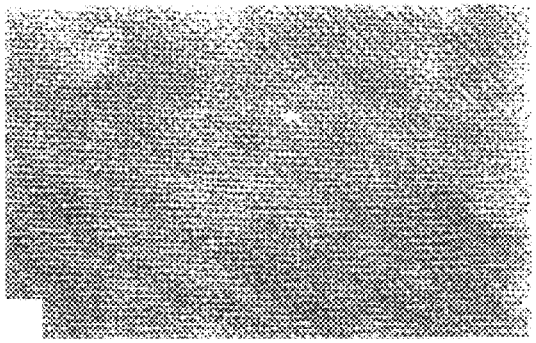
Figure 10C:
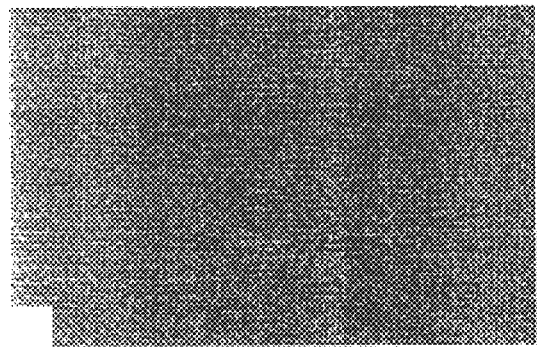
Figure 10D:
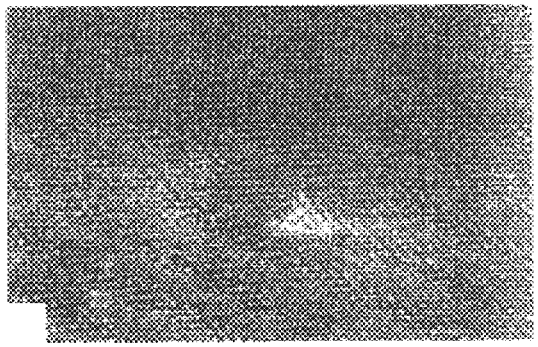
Figure 10E:
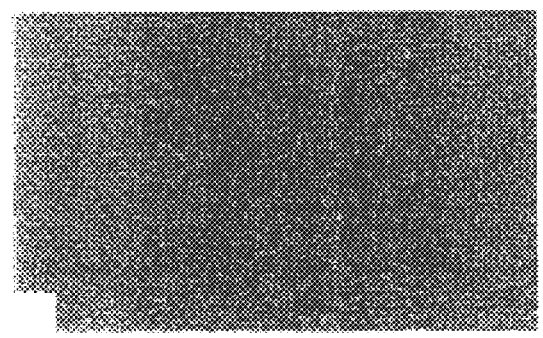
Figure 10F:
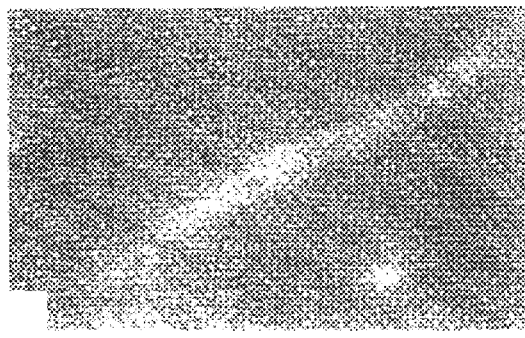

Herbimycin A attenuated the ability of PAO to increase protein tyrosine phosphorylation (FIG. 9), correlating with its effects on tight junction permeability (FIG. 8). This inhibitory effect of herbimycin A is consistent with PAO action via inhibition of tyrosine phosphatases and suggests that a tyrosine kinase inhibitor could be useful in modulation of tight junction permeability.

3. Anti-phosphotyrosine Label of Rat Brain Endothelial Cells after Middle Cerebral Artery (MCA) Occlusion (i) Stroke and Stroke Model Stroke is the result of reduced blood supply causing (usually) focal ischaemia in the brain. This can be caused by either the rupture of a blood vessel (haemorrhagic stroke) or due to blood vessel blockage by a blood clot (occlusive stroke). Recovery from stroke is compromised by development of oedema that begins soon after the initial insult, and continues for several days. This oedema, if widespread, causes increased intracranial pressure and can harm the brain, reducing the extent of recovery. The oedema seen in the first hours after stroke is likely to be cytotoxic, caused by swelling of cellular elements in the region of damage. However, oedema is still present for the next few days and this maintained oedema is vasogenic, i.e. the result of increased permeability of brain capillary endothelial cells. It is likely that the blood vessels with increased permeability are microvessels supplied by a different artery adjacent to the area of infarct, and it is possible that the endothelial cells liming these vessels respond to locally released factors from ischaemic tissue nearby. In this case agents that interfere with the action of these locally released factors are of potential therapeutic value in that they could prevent the loss of blood-brain barrier integrity, ameliorate that prolonged oedema after stroke and improve the extent and speed of recovery of the patient.

In humans, the most frequently encountered stroke syndrome is associated with infarction in the area of the territory of the middle cerebral artery (MCA). The MCA supplies blood to a large area of the cortex through surface branches and to several deeper structures through smaller penetrating branches. A commonly used in vivo model of severe stroke is MCA occlusion in adult rats.

Here, focal cerebral ischaemia was induced by permanent occlusion, by cauterization, of the left MCA of adult Sprague Dawley rats. After 24 hours, rats were either sacrificed with no further operation or were intravenously injected with Evan's blue dye (see below) 30 minutes before being sacrificed. The brain was removed immediately and frozen. The area of brain served by the MCA was visibly swollen 24 hours after occlusion.

(ii) Analysis of blood-brain barrier integrity

Evan's blue: The blood protein albumin is restricted to the lumen of vessels that have an intact blood-brain barrier, but when blood-brain barrier function is lost albumin leaves the vessels and enters the brain parenchyma. Evan's blue dye binds to albumin in the blood, and when albumin leaks into the tissues albumin-associated dye can be detected by fluorescence microscopy. Frozen sections of unfixed tissue were examined for Evan's blue extravasation into the brain parenchyma. MCA occlusion caused Evan's blue to leak into the brain parenchyma in part of the left cortex, this could be detected within 24 hours. Gross morphological changes in the labelled area indicated that the brain was severely damaged following the operation. Tissue away from the damaged area (e.g. in the right cortex) did not label with Evan's blue.

Albumin: Blood-brain barrier breakdown was also detected by incubating sections with antibody to rat albumin to demonstrate albumin leakage. Sections of brain labelled in this way also showed increased labeling of the parenchyma (outside the vessels), near the site of damage, whilst undamaged areas were again unlabelled, indicating a local loss of blood-brain barrier function at the sites affected by occlusion.

(iii) Effects of MCA occlusion on blood-brain barrier capillary endothelial cells As discussed previously, control of the level of protein tyrosine phosphorylation appears to be essential for the maintenance of functional tight junctions. Many (bioactive) factors act through receptors that can alter levels of tyrosine phosphorylation, either through changing the activity of tyrosine kinases or tyrosine phosphatases. If factors released during ischaemia increase endothelial cells permeability by a mechanism that depends on alteration of the level of protein tyrosine phosphorylation, then it is possible that their action could be controlled through drugs that prevent elevation of protein tyrosine phosphorylation. The advantage of this approach is, firstly, that if the increased permeability is caused by many factors acting through different pathways that converge at the control of tyrosine phosphorylation levels, then one drug could be used to control the action of many released factors. Secondly, effective treatment would not need to await the identification of the active agents and the subsequent development of specific antagonists.

In these experiments, brain sections were labelled with an antibody to phosphotyrosine (monoclonal antibody 4G10) and labelled with a polyclonal antibody to collagen type IV to outline blood vessels. In sham operated animals, 4G10 label was restricted to a few large, peripherally located, vessels with a pattern of staining consistent with tyrosine phosphorylation of proteins at the borders of cells lining the vessels. After 24 hours of MCA occlusion an increase in 4G10 label was seen associated with microvessels located at the edge of the severely damaged tissue (see FIG. 10). The increase in 4G10 label was restricted to vessels in the area of the lesion, but not every vessel was labelled. 4G10 distribution in the microvessels is similar to that seen when brain tissue from normal adult rat is exposed to pervanadate, a drug that elevates levels of phosphotyrosine by inhibiting the enzymes responsible for tyrosine dephosphorylation. However, pervanadate induces increased phosphotyrosine in both small and large blood vessels, whilst after 24 hours of MCA occlusion, only microvessels showed increase phosphotyrosine label.

In control experiments, 4G10 binding was prevented by perincubation of the antibody with phosphotyrosine indicating specific binding of 4G10 to phosphotyrosine.

The above data suggests that the level of tyrosine phosphorylation of proteins at brain microvessel endothelial cell borders is upregulated 24 hours after MCA occlusion. It is likely that blood-brain barrier leakiness seen after stroke is caused by release of factors from ischaemic tissue that act by elevation of endothelial cell protein tyrosine phosphorylation. Drugs that prevent phosphotyrosine elevation could reduce the loss of blood-brain barrier integrity that causes oedema following stroke, and hence prevent some of the ensuing permanent damage to neuronal cells.

In addition to the particular catenins discussed above it has also been found that other proteins—p100 and p120—which are associated with the catenin cadherin complex are tyrosine phosphorylated. These are discussed below:

Discussion of p100 and p120

Immunoblot analysis of a variety of different cells revealed that the anti-p120 monoclonal antibody 2B12 (Kanner et al., 1990) recognized a broad band of approximately 120 kDa. Another anti-p120 monoclonal antibody that had been raised against the C-terminal portion of p120 recognized the same as 2B12 and, in addition, another cluster of bands at 100 kDa. The reason for the multiplicity of bands at 120 kDa and 100 kDa is not clear, but obviously they are immunologically related. The pattern of appearance of these multiple bands also depended on the cell type. For example in MDCK cells, the bands were very diffuse, whereas in MDBK cells they were clearly resolved, especially when visualized by [$^{35}$S]methionine labelling in the absence of fluorographic reagent. It is possible that post-translational modification, such as phosphorylation and myristoylation may account for the appearance of multiple bands. The relationship, apart from the immunological one, between p120 and p100 is not yet clear. The Northern blots described by Reynolds et al. (1992) suggested the possibility of p120-related gene products or alternatively spliced transcripts. Furthermore, Southern analysis apparently indicated that one or more p120-related genes exist (Reynolds et al., 1992). It follows that the cluster of bands corresponding to p120 and the similar cluster to p100 could also represent splice variants of, respectively, p100 and p120. It is also possible that p100 could simply represent a degradation product of p120, although samples were prepared in denaturing buffer and immunoprecipitations were performed in the presence of inhibitors of a broad spectrum of proteases.

Figure 14:
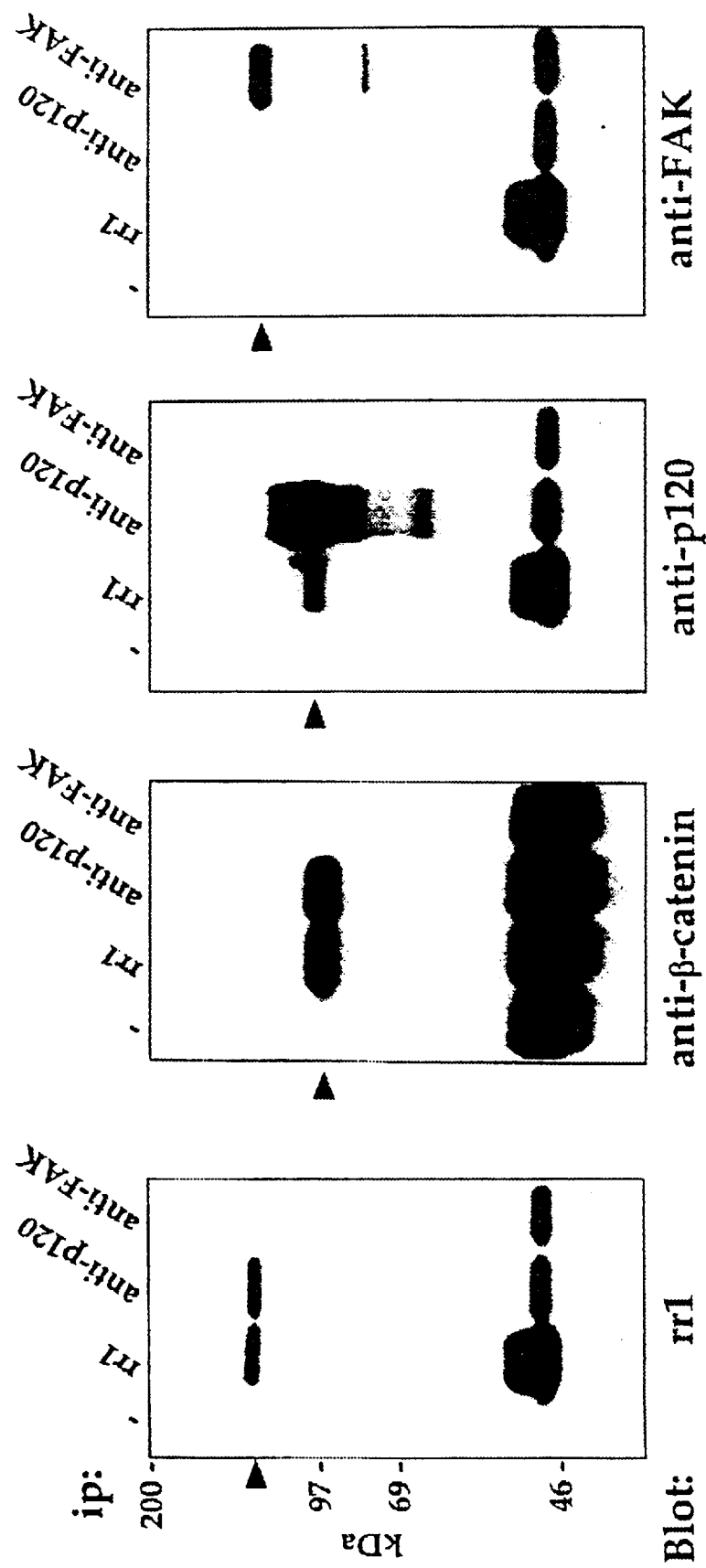
FIG. 14 shows the detection of anti-p120 reactive material in anti-E-cadherin immunoprecipitates and E-cadherin in the anti-p120 immunoprecipitates.
Figure 17A:
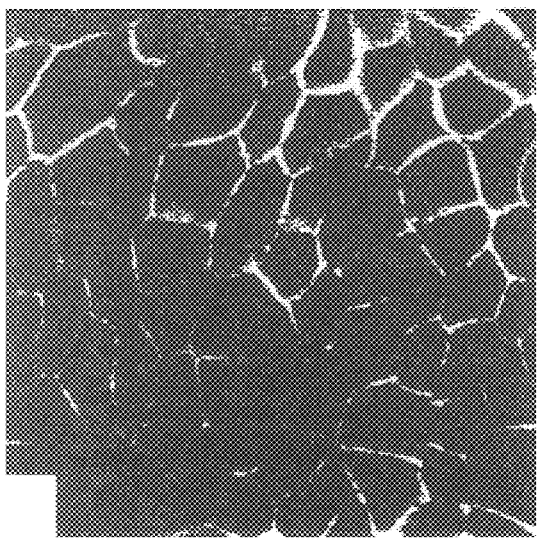
FIG. 17 shows the localisation of anti-p120 reactivity and β-catenin in MDCK cells, and brain endothelial cells.
Figure 17B:
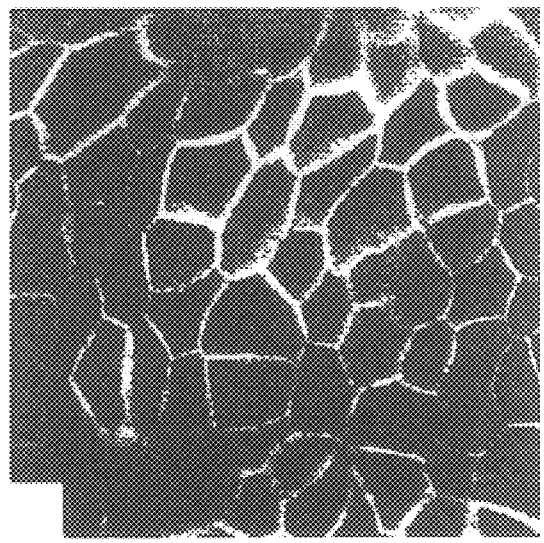
Figure 17C:
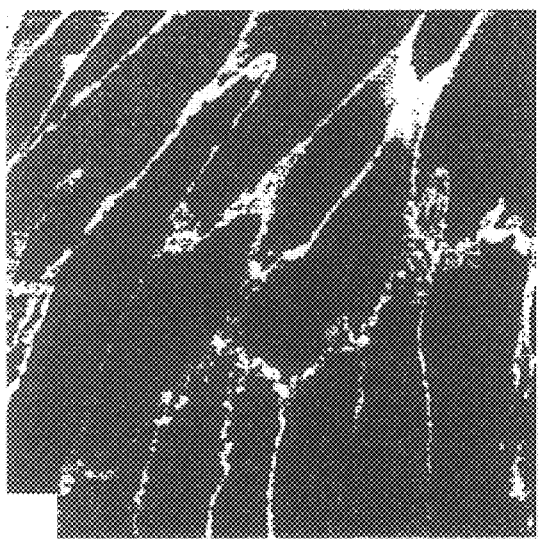
Figure 17D:
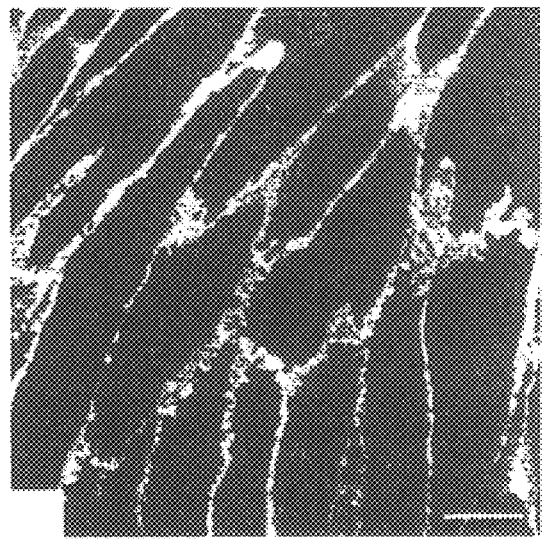
Figure 18A:
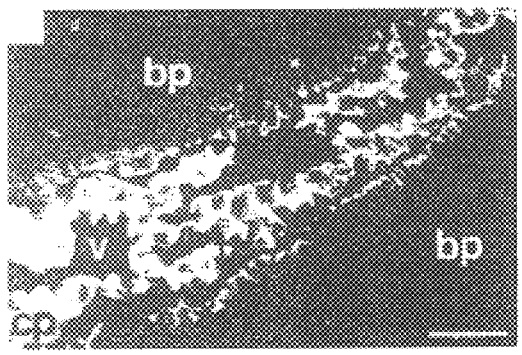
FIG. 18 shows the distribution of anti-p120 immunoreactivity in brain and skeletal muscle tissue of the rat.
Figure 18B:
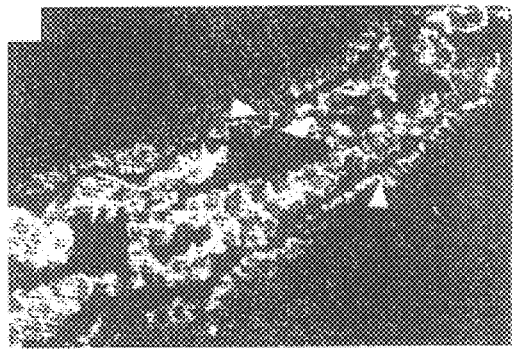
Figure 18C:
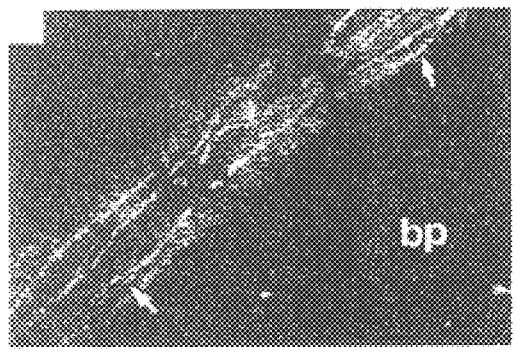
Figure 18D:
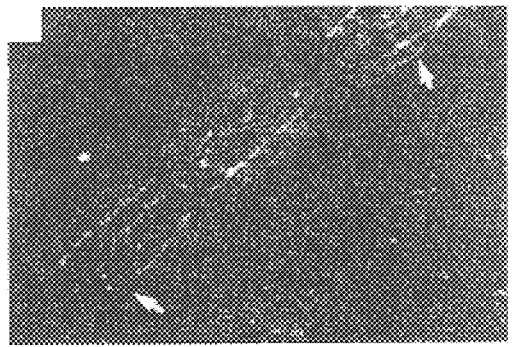
Figure 18E:
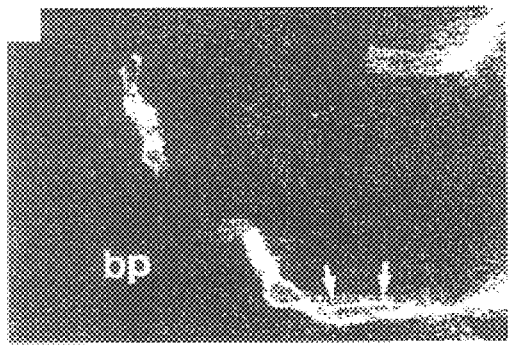
Figure 18F:
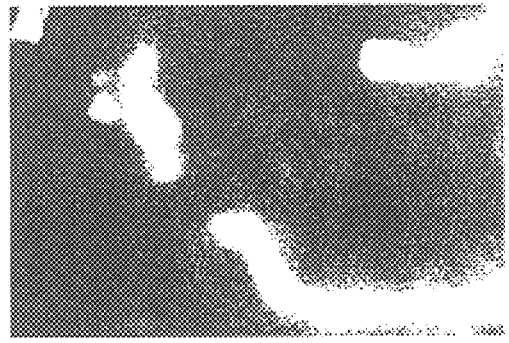
Figure 18G:
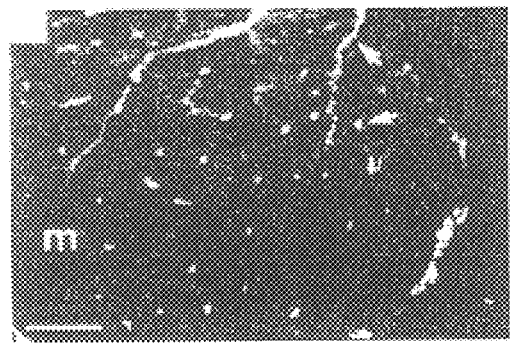
Figure 18H:
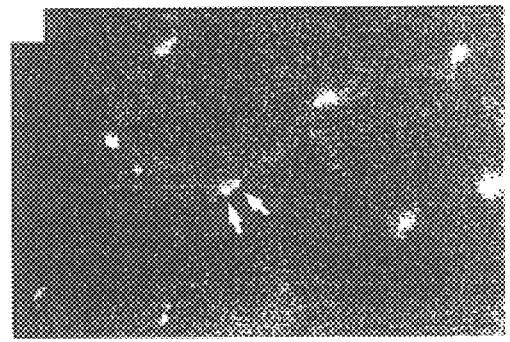

Our results provide evidence that p120/p100 associates with the cadherin/catenin complex. Thus, from TX-solubilized epithelial cells, anti-p120 antibody immunoprecipitated [$^{35}$S]methionine-labelled proteins that comigrated with those immunoprecipitated by cadherin antibodies (FIG. 13). Immunoblot analysis verified the identity of these proteins as cadherins and catenins (FIG. 14). Similarly, anti-p120 reactive protein was seen in the anti-E-cadherin immunoprecipitates from MDCK cells, although on the basis of mobility this appears to represent primarily p100, not p120 (FIG. 14). However, it should be noted that p120 immunoreactive protein was not unequivocally identified in the MDCK cells because of the poor reactivity of the 2B12 antibody with canine protein. This apparent association between p120/p100 and the cadherin/catenin complex was not restricted to epithelial cells as similar results were obtained using endothelial cells, both by [$^{35}$S]methionine-labelling (FIG. 15) and immunoblot analysis (FIG. 16). However, although our results clearly show an interaction between catenins and p120/p100 in endothelial cells, we did not identify a cadherin in the anti-p120 immunoprecipitates. The interpretation of the biochemical analyses of the protein complexes in the epithelial and endothelial cells is further supported by the immunocytochemical study. In cultured cells and in tissue sections, anti-p120 immunoreactivity was strongly associated with intercellular junctions, displaying a localization that was remarkably similar to that obtained with anti-β-catenin antibody (FIGS. 17 and 18). Here, we were restricted to using the anti-p120 antibody which might recognize either p120 or p100, or both.

Figure 11:
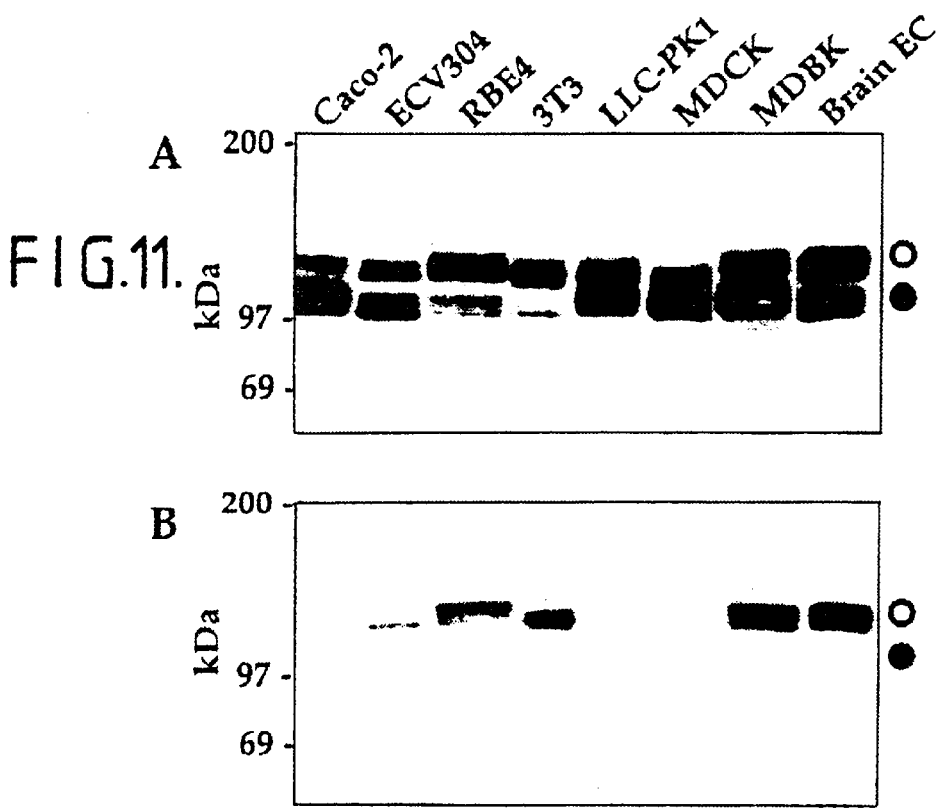
FIG. 11 shows the characterisation of anti-p120 and 2B12 immunoreactivity.

Of course, one explanation for the ability of anti-p120 antibody to immunoprecipitate the cadherin/catenin complex is that it cross-reacts with one of the known components of the complex. However, this is unlikely for the following reasons. TDS lysis of cells dissociates α-catenin and γ-catenin from the cadherin and β-catenin complex (see McCrea and Gumbiner, 1991). In anti-E-cadherin immunoprecipitates from MDCK cells lysed in TDS buffer, anti-p120 antibody failed to react with E-cadherin or the co-precipitating β-catenin. In anti-α-catenin immunoprecipitates from MDCK cells lysed in TDS buffer, anti-p120 antibody failed to react with α-catenin (results not shown). As shown in FIG. 16, β-catenin immunoprecipitates from TDS-lysed endothelial cells, although clearly containing β-catenin, and presumably a cadherin, did not contain any anti-p120 reactivity. Cross-reactivity with γ-catenin, a protein of approximately 85 kDa, is unlikely as the immunoblots shown in FIG. 11 fail to show reactivity with protein below 100 kDa.

One protein that has to be addressed concerns the lack of any obvious [$^{35}$S]methionine-labelled bands that correspond to p120/p100 in the cadherin immunoprecipitates from TX lysed cells. Thus, as shown in FIG. 13, rr1 and the anti-p120 immunoprecipitates from MDCK cells look remarkably similar. However, it is clear from the anti-p120 immunoprecipitates from TDS lysed cells that the anti-p120 reactive material migrates as a broad band, the bulk of which migrates between α- and β-catenin, with the remainder migrating slightly slower than α-carenin. In conjunction with the immunoblot analysis shown in FIG. 14, which demonstrates that only a fraction of the anti-p120 immunoreactive material is immunoprecipitated by rr1, and the fact that p120 contains about half of the number of methionenesin α- and β-catenin, if steady-state labelling is assumed, then it is obvious that it would be difficult to see any labelling corresponding to the anti-p120 immunoreactive material in the rr1 immunoprecipitates. Similarly, with respect to the experiments with the brain endothelial cells (FIG. 15), under the extraction conditions employed it appears that only a fraction of the pool of the cadherin/catenin complex associates with p100, and even less with p120. Thus, it would be difficult to see labelling of bands corresponding to p120 and p100 in the β-catenin immunoprecipitates as this region of the gel is already occupied by other major brands. It is also difficult to discern a band corresponding to the cadherin seen in the β-catenin immunoprecipitates in either the anti-p120 or 2B12 immunoprecipitates because of the dominance of the labelling of p120 (FIG. 15).

It is emphasized that there are also clear quantitative differences with respect to the ability of 2B12 and anti-p120 antibody to immunoprecipitate the cadherin/catenin complex. Due to poor reactivity of 2B12 with canine protein, this could not be addressed with MDC cells. In bovine brain endothelial cells, the anti-p120 antibody immunoprecipitated the cadherin/catenin complex, although not as well as anti-β-catenin antibody. 2B12 was even less effective than anti-p120. As anti-p120 recognizes p120 and p100, and 2B12 only p120, the difference in the amount of the complex immunoprecipitated must be attributable to greater association of p100 with the catenins. As far as we can tell, the efficiency of anti-p120 and 2B12 in immunoprecipitation was similar in this experiment (see FIG. 15 for the similar intensity of a band corresponding to p120in the anti-p120 and 2B12 immunoprecipitates from cells lysed in TX buffer). These data also indicate that independent complexes of p100 and p120 exist with catenins, rather that a catenin/p100/p120 complex. If the latter were the case, 2B12 would be expected to immunoprecipitate as much of the catenins as anti-p120 antibody.

Our early study provides a link between p120/p100 and adherens junction proteins. It is possible that such an interaction, perhaps via the influence of regulatory kinases, such as src, lyn and yes (see Tsukita et al., 1991), may play a role in the modulation of cadherin function, and thereby other cellular functions influenced by the adherens junction. With respect to phosphorylation, the tyrosine phosphate inhibitor phenylarsine oxide was found to cause an increase in tight junction permeability in MDCK cells (Staddon et al., *J. Cell Sci.* in press). This inhibitor increased the tyrosine phosphorylation of the anti-p120 immunoreactive material (a major p100 band, a minor p120 band) in these cells, as analyzed by anti-p210 immunoblotting of anti-p120 immunoprecipitates from SDS lysates (results not shown; see Staddon et al., *J. Cell Sci.* in press). The p120/p100 proteins could also be involved in the interaction between cadherins and the actin-based cytoskeleton, p120/p100 may also be part of a signaling cascade, communicating information about the state of cell-cell adhesiveness to the interior of the cell.

β-catenin is an arm protein (McCreas et al., 1991) and can associate with cadherins and the APC gene product (Rubinfeld et al., 1993; Su et al., 1993), also an arm protein (see Peifer et al. 1994). p120 is an arm protein (Reynolds et al., 1992; Peifer et al., 1994), and, as we describe here, p100 is an immunologically related protein. These proteins can interact with β-catenin. The exact nature of the interaction between p120/p100 and the catenins remains to be established. These proteins may interact directly, or associate with different regions of the cytoplasmic domain of cadherins. Other linking or intermediary binding proteins could also be involved. Clearly, there appears to be diverse interactions among arm proteins, suggesting the importance of the arm motif in intracellular signailing.

In summary, our studies identify p100 and p120-related protein. We present evidence that these proteins interact with the cadherin/catenin complex. Given the important role of the cadherin/catenin complex in cellular transformation and the identification of p120 as a pp60$^{src}$ substrate, this suggests that p120/p100 may play a role in cellular growth control and other processes. Such as tight junction permeability control, via an influence on cell-cell adhesion.

Other groups have also observed increased tyrosine phosphorylation of components of the cadherin/catenin complex, but under conditions that differ from those described here. In pp60$^{v-src}$ transfected rat 3Y1 cells, a fibroblast cell line, vanadate induced the tyrosine phosphorylation of E- or P-cadherin and β-catenin (Matsuyoshi et al, *J. Cell Biol.* 118 703–714 (1992)). In chicken embryo fibroblasts, pp60$^{v-src}$ caused the tyrosine phosphorylation of N-cadherin and α- and β-catenin. pp60$^{v-src}$ activity in MDCK cells resulted in a rapid (10–30 min) tyrosine phosphorylation of E-cadherin and β-catenin (Behrens et al, *J. Cell Biol.* 120 757–766 (1993)). Behrens et al (1993) also reported that pp60$^{v-src}$ resulted in a decrease in TER of MDCK cells. However, the decrease in TER was observed several hours after tyrosine phosphorylation of E-cadherin/β-catenin. Furthermore, pp60$^{v-src}$ resulted in a major alteration in cell morphology, from epithelial to fibroblast-like. The results of Behrens et al (1993) differ from the present results in that a very rapid decrease in TER is shown here in the absence of any gross changes in cell morphology.

Our data suggest that the tyrosine phosphorylation of components of the cadherin/catenin complex (particularly β-catenin), and/or of certain proteins associated with this complex (particularly p120 and a protein referred to herein as "p100"), may serve to regulate acutely the permeability of the tight junction. Thus, intracellular kinase-mediated tyrosine phosphorylation, like the removal of extracellular Ca²⁺, may led to a rapid uncoupling of the adherens junction. Consequently, this leads to an opening of the tight junction.

The conserved cytoplasmic domain of cadherins is known to associate with three proteins, termed α-, β- and γ-catenin (Ozawa et al., 1989), which serve to link cadherins to the actin-based cortical cytoskeleton (Hirano et al., 1987). The association of cadherins with catenins is essential for intercellular Ca2+-dependent adhesiveness (Nagaruchi and Takeichi, 1988; Ozawa et al., 1991; Kintner, 1992). α-catenin is homolgous to vinculin (Herrenknect et al., 1991; Nagafuchi et al., 1991), making it a good candidate for interaction with the actin-based cytoskeleton (see Ozawa et al., 1990; Hirano et al., 1992). β-catenin is homologous to the Drosophila segment polarity gene armadillo, suggesting a role in developmental signalling in vertebrates (McCrea et al., 1991), γ-catenin is probably identical to plakogiobin (Knudsen and Wheelock, 1992; but see Piepenhagen and Nelson, 1993), which again is homologous to armadillo (see Franke et al., 1989; Peifer and Wieschasu, 1990). Indeed, β-catenin and plakoglobin appear to form a multigene family (Peifer et al., 1992).

A repeating 42 amino acid motif that was originally identified in armadillo (Riggleman et al., 1989) has also been found in several other proteins, including β-catenin and plakoglobin, with a variety of functions (Peifer et al., 1994). These include the APC gene product, a tumour suppressor protein (Kinzler et al., 1991), p120, a pp60$^{src}$ substrate (Reynolds et al., 1992), smgGDS, an exchange factor for ras-related G proteins (Kikuchi et al., 1992), a suppressor of RNA polymerase I mutations in yeast (Yano et al., 1192; 1994) and band 6 protein, a major desmosomal constituent (Hatzfeld et al., 1994). The function of the repeats in these arm proteins is unknown. Interestingly, the APC gene product associates with β-catenin (Rubinfeld et al., 1993; Su et al., 1993), supporting an important role for catenins in intracellular processes that regulate cell growth. Furthermore, this illustrates that cadherins are not exclusive cellular partners of catenins, raising the possibility of other interactions among catenins, cadherins and arm proteins, important in a variety of biological processes.

p120 was initially identified as one of several substrates of the tyrosine kinase pp60$^{STC}$ (Reynolds et al., 1989; Kanner et al., 1990). It is membrane-associated and can be myristoylated, but does not appear to be glycosylated (Kanner et al., 1991). Mutational analysis suggested that tyrosine phosphorylation of p120 is necessary for that of pp60$^{STC}$-mediated cellular transformation (Linder and Burr. 1988; Reynolds et al., 1959). Tyrosine phosphorylation of p210 was also observed in response to epidermal growth factor, platelet-derived growth factor, colony-stimulating factor 1 and in polyoma virus middle T antigen-transformed cells (Downing and Reynolds, 1991; Kanner et al., 1991), but the exact role of p120 in cellular physiology and pathology remains to be established.

Our data suggest that the permeability of tight junctions is crucially dependent upon the balance of tyrosine kinase(s) and tyrosine phoslohatase(s) that determine the phosphorylation of the cadherin/catenin complex and/or of certain proteins associated therewith. Appropriate stimulation of a tyrosine kinase (or inhibition of tyrosine phosphatases) should, therefore, open up the blood-brain barrier or other barrier involving tight junctions. Conversely, inhibition of endothelial cell tyrosine kinase (or activation of tyrosine phosphatases) would lessen, say, the amount of oedema that results from increased blood-brain barrier leakiness following stroke and lessen or prevent cedema associated with brain tumours. Similarly, during situations involving cell trafficking across the blood-brain barrier, inhibition of endothelial tyrosine kinase should prevent cell migration.

Available tyrosine kinase inhibitors include: genistein, herbimycin A, lavendustin A; methyl 2,5-dihydroxycinnamate; staurosporine and tyrphostins.

Tyrosine kinase activators include various ligands, such as FGF, PDGF and VEGF, which activate receptors that couple to appropriate tyrosine kinases. Also, it may be that, during ischaemia, a ligand is released from glial or neuronal cells which activates an endothelial cell tyrosine kinase, thereby causing opening of the blood-brain barrier; a blocker of this ligand would be particularly useful in stroke therapy.

Tyrosine phosphatase inhibitors include vanadate and phenylarsine oxide, of which the latter is preferred because of its more specific activity.

Agents which promote tyrosline protein dephosphorylation, and therefore promote closure of a physiological barrier such as the blood-brain barrier are useful in a number of ways. Such a medicament may be useful in decreasing brain oedema following stroke or associated with brain tumours and/or in blocking the entry into the brain of both leukocytes that mediate an immune response, such as occurs in multiple sclerosis, and metastatic cancer cells that may form tumours, Such a medicament may also be useful in promoting tyrosine protein dephosphorylation in peripheral endothelial cells to prevent or mitigate peripheral oedema such as high altitude pulmonary oedema. A further use for such a medicament would be in promoting tyrosine protein dephosphorylation in gastric epithelial cells to treat gastric ulcer, which may be exacerbated by loose tight junctions (Ohkusa et al. Gut 34 86–89 )1993)).

Agents which promote tyrosine protein phosphorylation, and therefore promote opening of a physiological barrier such as the block-brain barrier are also useful in a number of ways. Such a medicament may be useful in promoting peripheral endothelial cell tyrosine protein phosphorylation to increase delivery of chemotherapeutic agents to peripheral tumours. (Although peripheral tumours do not have a barrier as tight as the blood-brain barrier, the centre of the tumour is often less well vascularised.) Such a medicament may also be useful in promoting pulmonary epithelial cell tyrosine protein phosphorylation, preferably when the medicament is administered using an inhaler, so that tight junctions become leaky to fluid, which can then act to dilute the accumulation of mucous in the airways.

According to a third aspect of the invention, there is provided the use of an agent which promotes tyrosine protein phosphorylation and the use of a blood-brain barrier- or other physiological barrier-impermeant drug in the preparation of a medicament for delivering the drug to the brain or other part of the body across the barrier.

The drug may be any pharmaceutically, veterinarily or diagnostically useful compound or composition of compounds which is normally impermeant to the block-brain or other physiological barrier or at least insufficiently permeant. The pharmacological nature of the drug is otherwise unimportant. The invention is thereofore useful in the delivery of a wide range of drugs across physiological barriers such as the blood-brain barrier. However, it is anticipated that among the primary candidates for delivery by means of this aspect of the invention will be: anti-tumour compounds, such as methotrexate, adriamycin and cisplatin; growth factors, such as NGF, RDNF and CNTF, which are used to treat neurodegenerative disease; imaging agents, especially those that are antibody based; and neurotransmitter antagonists or agonists which do not penetrate the blood-brain barrier (such as certain NMDA receptor blockers).

According to a fourth aspect of the invention, there is provided a composition comprising an agent which promotes tyrosine protein phosphorylation and a drug to be delivered across a physiological barrier such as the blood-brain barrier. The composition may also contain a pharmaceutically or veterinarily acceptable carrier.

In addition to being useful in the delivery of drugs across physiological barriers such as the block-brain barrier, the invention may also useful in preventing certain unwanted drugs crossing the barrier, if their transit across the barrier is by way of tight junctions.

Compositions of, and agents useful in, the invention may be adapted for administration by any suitable means, enteral or parenteral. Compositions for parenteral administration, such as injection or infusion, will generally be sterile. The dosage of any particular agent will depend on a number of factors and is likely to be optimised in experimental or clinical trials. In any event, the appropriate dosage for a particular patient or subject will be determined by the responsible physician or clinician in each case.

Preferred features of each aspect of the invention are as for each other aspect, *mutatis mucandis*.

The invention will now be illustrated by way of example only. In the following Examples the materials and methods discussed below are utilised.

EXAMPLES

Materials and Methods For Examples 1 to 10

Materials and reagents

Tissue culture-treated, polycarbonate Transwell filters (0.4 $\mu$M) were from Costar. All tissue culture materials were from Gibco except for plasma-derived horse serums which was from Lamoire Biological Laboratories (Pipersville, Pa.). Vanadate was from Sigma and phenylarsine oxide (PAO) was from Kodak, Gel electrophoresis reagents were from Bio-Rad. Other reagents used were of the highest grace commercially available.

Antibodies

Antibodies against $\alpha$- and $\beta$-catenin were raised in rabbits using synthetic peptides coupled to keyhole limpet haemocyanin (Pierce) by glutaraidehyde. The peptide for $\alpha$-catenin corresponded to amino acids 890–901 of mouse $\alpha$E-catenin (Herrenknecht et al., 1991), the pepdde for $\beta$-catenin to amino acids 751–781 of mouse $\beta$-catenin (Butz et al., 1992). The $\beta$-catenin peptide contained an addition C-terminal lysine for coupling, which is not in the protein. After several rounds of intradermal and subcutaneous immunisations in intervals of 3 weeks using the Ribi adjuvant system (RIBI Immunochem Research, Inc.), specific antibodies were isolated by affinity chromatography on peptide -$\epsilon$-carboxyhexanoyl (ECH)-Sepharose (Pharmacia) columns (6 and 15 mg of $\alpha$-catenin and $\beta$-catenin peptide, respectively, coupled to 1 of ECH-Sepharose 4B as described by Pharmacia).

The rat monoclonal and-ZO-1 antibody (R40.76) was from Dr. Bruce Steveruon (Department of Anatomy and Cell Biology, University of Alberta, Edmonton, Canada). The mouse monoclonal anti-E-cadherin antibody rr1 was from Dr. Barry Gumbiner (Memorial Sloan-Kettering Cancer Center, New York, N.Y.). Rat monoclonal anti-$\alpha$-catenin ($\alpha$-18) was from Prof. Shoichiro Tsuldta and Dr. Akira Nagaruchi (Department of Information Physiology, National Institute for Physiological Sciences, Okazaki, Japan). Monoclonal anti-phosphotyrosine antibody PY20 was from ICN Biomedicais. Horseradish peroxidade-conjugated anti-phosphotyrosine antibody RC20 H was from Tramduction Laboratories. Phosphotyrosine antibody (4G10) conjugated to agarose was from Upstate Biotechnology Inc. FITC-conjugated goat anti-rat and anti-mouse IgG were from Jackson Immunoresearch Laboratoried Ltd.

Cell culture

All cells were maintained at 37° C. under 5% $CO_2$ in humidified air. MDCK cells (strain 1), from Dr. Barry Gumbiner, were maintained in MEM containing 10% FCS. For experimental use, $10^5$ cells in 0.2 ml of medium were plated on 6.5 mm Transwell filters. The basolateral chamber contained 0.75 ml of medium. The cells were used between 4 and 7 days after plating.

Primary cultures of bovine brain endothelial cells were prepared essentially as described by Rubin et al. (1991). The cells were continuously grown in 30% astrocyte-conditioned medium. After plating $2.5 \times 10^4$ cells on 6.5 mm, collagen-coated Transwell filters, the cells were maintained for 2–3 days in the absence or presence of 250 $\mu$M 8-(4-chlorophenylthio)cAMP (CPT-cAMP) plus 17.5 $\mu$M of the phosphodiesterase inhibitor Ro20-1724 (Calbiochem), as described by Rubin et al. (1991).

Experimental protocol and resistance measurements

For experiments involving MDCK cells, culture medium was replaced with MEM containing 0.5% calf Serum for at least 2 hours prior to use. With the brain endothelial cells, additions were made directly to the medium in which the cells were cultured. Initial resistance measurements were taken using a Millicell-ERS resistance system (Millipore). Aqueous solutions were added to the apical and basolateral chambers of the Transwell from 100-fold concentrated stock solutions. Vanadate was prepared as a 0.1 M stock solution, pH 7. PAO was dissolved in DMSO and added directly to the medium from a 1000-fold concentrated stock. Resistance measurements were subsequently taken as indicated. In all cases, appropriate solvent controls had no effect on resistance.

Paracellular flux

Culture medium was replaced by bicarbonate-free, Hepes-buffered MEM (ICN Biomedicals) containing 0.5% calf serum (0.1 ml/apical chamber; 0.5 ml/basciateral chamber), and the Transwells were then incubated for 2 hours under a humidified air atmosphere at 37° C. it was verified that the switch to culture medium in itself did not affect the resistance of the MDCK cells. Additions were made to the chambers as indicated, and immediately 1 $\mu$Ci of [U-$^{14}$C]sucrose (621 Ci /Mol; Amersham) in 10 $\mu$l of culture medium was added to the apical chamber. The Transwells were then shaken at setting 4 on a Lucklam R100 rotary shaker (Denley Instruments Ltd., West Sussex. UK), and aliquots of the basolateral chamber were removed at the indicated times for scintillation counting.

Immunocytochemistry

Cells were fixed in 3 pararormaldehyde made up in PBS containing 0.5 mM $CaCl_2$ and 0.5 mM $MgSO_4$. After 15 minutes at room temperature, the fixed cells were washed and then permeabilized by incubation with 0.5%. Triton X-100 in PBS for 10 minutes. After washing, the cells were incubated for 30 minutes in PBS containing 10% calf serum plus 0.1 M lysine, pH 7.4. Incubation with primary antibody was in PBS containing 10% calf serum for either 1 h at room temperature or overnight at 4° C. After washing, the cells were then incubated for 30–60 minutes at room temperature with a 1:1000 dilution of FITC-conjugated goat anti-mouse or anti-rat IgG, as appropriate, in PBS containing 10% calf serum. When required, rhodamine phalloidin (2 U/ml; Molecular Probes, Inc.) was included with the secondary antibody. After washing, the filters were mounted with Citfluor (Citifluor Products, Canterbury, UK) and examined using a Nikon Microphot-FXA fluorescence microscope fitted with 40× and 60× objectives. Photographs were taken using Kodak T-MAX film (400 ASA).

Immunoprecipitation

Confluent monolayers of cells on 24 min Transwells were washed with ice-cold PBS (containing 0.9 mM $CaCl_2$ and 0.5 mM $MgCl_2$). After lysis in 0.5 ml of the appropriate buffer, the filters were gently scraped and the lysate was then centrifuged at 14,000× g. The supernatant was precleared with 10% (w/v) Protein A-Sepharose in lysis buffer for 15 minutes. Appropriate primary antibodies were added to the lysate and the immune complex was isolated using rabbit secondary antibodies, as necessary, and Protein A-Sephrose. The beads were washed five times with lysis buffer, and bound protein was solubilized in SDS-sample buffer (Laemmli, 1970) followed by heating at 100° C. for 5 minutes.

The protein inhibitors used were: leupeptin 10 μg/ml; $\alpha_2$-macroglobulin, 0.1 U/ml; soybean trypsin inhibitor, 10 μg/ml; PMSF, 1 mM. The cadherin/catenin complex was isolated at 4° C. using buffer comprising: 20 mM imidazole, pH 6.8; 100 mM KCl; 10mM EGTA: 2 mM $MgCl_2$; 300 mM sucrose; 0.2% Triton X-100; 1 mM vanadate; 1 mM Naf; 25 μM PAO; 0.02% $NaN_3$; protease inhibitors. Denatured proteins were isolated by immunopreciptiation after lysing the cells in: 1% SDS; Hepes, pH 7.4; 25 mM NaF; 1 mM vandata; 25 μM PAO; 2 mM EDTA. The lysates were heated for 5 minutes at 100° C. DNA was shared using a 23 G needle and the sample was then diluted into 2 ml of ice-cold buffer comprising: 3% Triton X-100; 0.1 M Nacl; Hepes, pH 7.4; 4.25 mM Naf; 1 mM vanadate; 25 μM PAO; 2 mM EDTA; protease inhibitors. ZO-1 and associated proteins were isolated at 4° C. essentially as described by Cumbiner et al. (1991) using buffer comprising: 1% Triton X-100; 0.5% sodium deoxycholae; 0.2% SDS; 0.15 M NaCl; 10 mM Hepes, pH 7.4; 25 mM NaF; 25 μm PAO; 2 mM EDTA; protease inhibitors.

Electrophoresis and immunoblotting

Whole cell lysates were prepared by rapidly replacing the culture medium with SDS sample buffer (Laemmli, 1970) followed by heating at 100° C. for 5 minutes. Cell extracts or immunoprecipitates in SDS sample buffer were resolved by SDS-PAGE (Laemmli, 1970). The slab gels were then equilbrated in buffer comprising: 48 mM Tris, 39 mM glycine, 20% methanol and 0.03% SDS. Proteins were trasferring to nitrocellulose filters (Hybond ECL; Amersham) which were Ponceau S stained and then blocked in 5% non-fat dried milk in PBS. After washing in PBS containing 0.05% Tween-20, the filters were probed with horseradish peroxidate-conjugated anti-phosphoryosine antibody (RC20H) or other unconjugated antibodies as described. After washing, unconjugated antibody was reacted with the appropriate horseradish peroxidase-conjugated secondary antibody. The filters were then extensively washed and immunoreactive bands were detected by enhanced chemiluminescence (Amersham) following the manufacturer's instructions.

Materials and Methods For Examples 11 to 18
Antibodies

The anti-canine E-cadherin antibody rr1 developed by Gumbiner and Simons (1996) was provided by Barry Gumbiner (Memorial Sloan-Kettering Cancer Center, NY) or obtained from the Developmental Studies Hybridoma Bank maintained by the Department of Pharmacology and Molecular Sciences, Johns Hopkins University School of Medicine, Baltimore, Md. 21205, and the Department of Biological Sciences, University of Iowa, Iowa City, Iowa 52242, under contract N01-HD-2-3144 from the NICHD. The anti-human E-cadherin antibody HECD-1 (Shimoyama et al., 1989) was from Takara Biomedicals (Shiga, Japan). Anti-p120 and anti-focal adhesion kinase (FAK) antibodies were from Transduction Laboratories (Lexington, Ky.). The anti-p120 antibody 2B12 (Kanner et al., 1990) was a gift from J. T. Parsons (University of Virgina, Charlottesville, Va.). The peptide-directed antibodies against α-and β-catenin (Staddon et al., *J. Cell Sci.* in press) were kindly provided by Kurt Herrenknecht (Eisai Research Laboratories Ltd., University College London, London UK). All secondary antibodies used for immunoprecipitation and immunocytochemistry were from Jackson Laboratories Inc. (West Grove, Pa.). HRP-conjugated secondary antibodies used for immunoblotting were from Amersham (Buckinghamshire, UK).

Cells

The following cells were cultured at 37° C. in medium containing 100 U/ml penicillin and 100 μg/ml strepomycin; Caco-2 (epithelial cells derived from a human colonic tumour: 5% $CO_2$, MEM, 10% FCS, 1% non-essential amino-acids 1 μg/ml insulin); ECV304 (a cell line derived from human vein endothelial cells: 5% $CO_2$, M199, 10% FCS); LLC-PK1 (epithelial cells derived from porcine kidney: 5% $CO_2$, M199, 10% FCS); MDBK (epithelial cells derived from bovine kidney: 5% $CO_2$, MEM10% FCS); Strain I MDCK cells (epithelial cells derived from canine kidney: 5$CO_2$, MEM, 10% FCS); RBE4 cells (immortablized rat brain endothehal cells (see Duneu-Trautmam et al., 1993):5% $CO_2$, α-MEM: Ham's F10 (1:1), 10% FCS, 0.3 mg/ml geneticin, 1 ng/ml bFGF); Swiss 3T3 fibroblasts (10% $CO_2$, DMEM, 10% FCS). Caco-2, EVC304, CCL-PK1 and MDBK cells were obtained form the European Collection of Animal Cell Cultures (Salisbury, UK), MDCK cells were provided by Barry Gumbiner, RBE4 cells were from Pierre Couraud (UniversitéParis VII, Paris, France) and Swiss 3T3 fibroblasts were Enrique Rozengutt (Imperial Cancer Research Fund, London, UK). Human umbilical vein endothelial cells were from Clonetics (Palo Alto, Calif.) and culture according the manufacturer's instructions. Primary cultures of Bovine or porcine brain endothelial cells were grown as described by Rubin et al. (1991). For experimental purposes, confluent cultures of Caco-2, MDBK, MDCK and brain endothelial cells were established on tissue culture-treated, polycarbonate Transwell filters (polycarbonate, 0.4 μm; Costar, Cambridge, Mass.). Other cells were grown on tissue culture plastic.

Immunoblotting and Immunoprecipitation

Whole cell lysates from cultures maintained for 16–20 hours in 0.5% serum were prepared by rapidly replacing the medium with hot Laemmli sample buffer (Laemmli, 1970) supplemented with 5 mM EDTA, followed by heating at 100° C. for 5 minutes. Proteins were resolved by slab-gel electrophoresis as described by Laemmli, (1970). The gels were equalibrated in buffer containing 48 mM Tris, 39 mM glycine, 0.03% SDS (w/v) and 20% methanol (v/v), and then transferred to nitrocellulose filters (Hybond, ECL, Amersham). After Ponceau S staining, the filters were blocked in 5% (w/v) non-fat dried milk in PBS at 4° C. for 16–18 hours. Filters were then incubated with primary antibody in PBS containing 0.05% Tween-20 and 1% BSA, followed by detection with appropriate HRP-conjugated secondary antibody and chemiluminescence (ECL, Amersham).

Immunoprecipitations were performed at 4° C. Cultures were rinsed with PBS and then lysed in either TX buffer (1% (v/v) Triton X-100, 25 mM Hepes, 2 mM EDTA, 0.1 M Nacl, 25 mM Naf, 1 mM vanadate, 25 µM phenylarsine oxide, pH 7.6 (adjusted with NaOH), 1 mM PMSF, 10 µg/ml soybean trypsin inhibitor, 0.1 U/ml $\alpha_2$-macroglobulin, 10 µg/ml leupeptin) or TDS buffer, which was identical to the TX buffer except that it was supplemented with 0.5% (w/v) sodium deoxycholate and 0.2% (w/v) SDS. The cells were incubated with lysis buffer for 10–15 minutes and then scraped. The lysates were collected and centrifuged at 14,000× g for 20 minutes. The supernatant was precleared with Protein A Sepharose (Pharmacia, UK) for 1–2 hours and then incubated with primary antibody for 1 hour followed by a further 1 hour with Protein A Sepharose alone, in the case of rabbit antibodies, or together with rabbit anti-mouse antibodies for the mouse monoclonal antibodies. After five washes in lysis buffer, immune complexes were dissociated by addition of Laemmli sample buffer followed by heating at 100° C. for 5 minutes. Protein analysis was by SDS-PAGE and immunoblotting as described above.

For [$^{35}$S]methionine labelling, the cultures were washed twice in methionine-free MEM supplemented with 0.5% FCS. The cells were incubated for 16–18 hours in this medium containing 50 µC/ml [$^{35}$S]methionine (>1000 Ci/mmol, Amersham). Protein analysis was by SDS-PAGE, followed by fixation in 25% methanol/10% acetic acid. Labelled protein was detected either by direct autoradiography at room temperature or by fluorography at −80° C. following impregnation of the gel with Amplify (Amersham).

Immunocytochemistry

Cells were fixed at room temperature for 15 minutes in 3% paraform-aldehyde made up in PBS containing 0.5 mM $CaCl_2$ and 0.5 mM $MgSO_4$. Fixed cells were washed and then permeabilized by incubation with 0.5% Triton X-100 in PBS for 10 minutes. After washing, the cells were incubated for 30 minutes in PBS containing 10% calf serum and 0.1 M lysine, pH 7.4. Incubation with primary antibody was in PBS containing 10% calf serum for 1 hour. After washing, the cells were then incubated for 30–60 minutes with a 1:100 dilution of fluorophore-conjugated anti-mouse or anti-rabbit IgG, as appropriate, in PBS containing 10% calf serum. After washing, the filters were mounted with Citifluor (Citifluor Products, Canterbury, UK) and examined using a Nikon Microphot-FXA fluroescence microscope fitted with 40× and 60× objectives. Photographs were taken using Kodak T-MAX film (400 ASA).

For the preparation of cryosections, brain and skeletal muscle from $CO_2$-asphyxiated rats were removed and rapidly frozen in liquid nitrogen. Tissue blocks were mounted in Tissue Tek (R. Lamb, London, UK) and sections of 5–10 µm thickness were cut one a Bright cryostat, air-dried and stored for up to 4 weeks at −20 ° C. After thawing, the sections were fixed and permeabilized as described above. The sections were then washed, blocked with PBS containing 10% calf serum for 15 minutes and incubated with primary antibody diluted in PBS containing 10% calf serum for 2 hours. After washing, they were incubated with PBS containing 10% calf serum with either 10% goat serum or 10% donkey serum, as appropriate of the host of the secondary antibody, for 15 minutes. They were then incubated with secondary antibody diluted in PBS and serum for 1 hour. Sections were washed, mounted and examined as described above.

Example 1

Pervanadate decreases the transcellular electrical resistance of MDCKI cells. Strain I MDCK cells were grown on 6.5 mm, 0.4 µm pore, TRANSWELL™ filters (Costar Catalogue No. 3413). The cells were plated at $10^5$ per filter and incubated for 4–7 days at 37° C. in a humidified 5% $CO_2$ incubator. Under these conditions the strain I MDCK cells gave transcellular electrical resistance values of 2000–5000 $\Omega$-$cm^2$. In the experiment whose results are shown graphically in FIG. 1a, vanadate was added (as the sodium salt pH7), to a final concentration of 0.01 mM (■) 0.1 mM (●) or 10 mM (▲) Transcellular electrical resistance (TER) was measured, with respect to control cells (□), using the MILLICELL-ERS™ system from Millipore (UK) Limited at the times indicated. After 3 hours, $H_2O_2$ was added to a final concentration of 2 mM (arrow). In the experiment whose results are shown graphically in FIG. 1b, vanadate and $H_2O_2$ were preincubated prior to addition to the cells and excess $H_2O_2$ was removed by catalase. The pervanadate was then added to the cells to give a final concentration of 0.01 mM (■), 0.03 mM (●) or 0.1 mM (▲), and TER was determined with respect to control cells (□) and cells to which the $Ca^{2+}$ chelator BAPTA was added (○, 2.5 mM final concentration). In the experiment whose results are shown in FIG. 1c, the cells were incubated with 0.1 mM (■) or 1.0, M vanadate (●), and TER was determined with respect to control cells (□). In all cases, the resistance values have been expressed relative to the initial resistance.

Example 2

Phenylarsine oxide decreases the transcellular electrical resistance of MDCK I Cells. Stain I MDCK cells were grown on TRANSWELL filters under the conditions described in Example 1. In the experiment whose results are shown graphically in FIG. 2a, phenylarsine oxide was added to a final concentration of 1 µM (■), 3 µM (●), 10 µM (▲), or 30 µM (♦) and the TER was expressed relative to the control cells (□). In the experiment whose results are shown graphically in FIG. 2b phenylarsine oxide (PAO) or BAPTA was added to a final concentration of 10 µM and 3 mM, respectively, to cells that had been preincubated for 10 minutes with 200 µM β-mercapoethanol (βME) or 100 µM 2,3-dimercaptopropranol (DMP). TER was determined 30 minutes later. The values shown are the mean ±S.D. of values derived from triplicate TRANSWELL filters, except for the BAPTA measurements which were the average of two filters. Pervanadate (PV) was added to a final concentration of 0.1 mM to cells that had been preincubated for 10 min in the absence or presence of 500 µM β-mercaptoethanol or 250 µM 2,3-dimercaptopropanol. TER was determined 30 minutes later. The values shown are the means of determinations from two TRANSWELL filters.

Example 3

Reversibility of the decrease in transcellular electrical resistance induced by the tyrosine phosophatase inhibitors. Strain I MDCK cells were grown as described in Example 1 on TRANSWELL filters. In the experiments whose results are shown in FIG. 3a, the cells were treated in the absence (●) or presence of 100 µM pervanadate (■,▲,●) 2,3-Dimercaptopropanol (250 µM) was added 10 min (■) , 20 min (▲) or 30 min (●) after pervanadate. TER was determined at the times indicated. In the experiment whose results are shown in FIG. 3b, the cells were treated in the absence (□) or presence of 10 µM phenylarsine oxide (■,●, ▲). Dimercaptopropanol 100 µM) was added 15 min (■), 30 min (●) or 45 min (▲) after phenylarsine oxide. TER was determined at the times indicated. The values shown (means ±S.D. of triplicate TRANSWELL filters) have been expressed relative to the initial TER.

Example 4

Pervanadate and phenylarsine oxide decrease the transcellular electrical resistance of brain capillary endothelial cells. Bovine brain capillary endothelial cells were grown on TRANSWELL filters and treated for two days in the absence (FIGS. 4b and 4d) or presence (FIGS. 4a and 4c) of CPT-cAMP/Ro20-1724, as described by Rubin et al, *J. Cell Biol.* 115 1725–1735 (1991). The data in FIGS. 4a/4b and FIGS. 4c/4d were derived from two independent preparations of cells, giving different initial resistance values. In FIGS. 4a/4b, the cells were incubated in the absence (□) or presence of 1 $\mu$M (■), 3 $\mu$M (●) , 10 $\mu$M (▲), 30 $\mu$M (♦) or 100 $\mu$M (▼) pervanadate. TER was determined at the times indicated. In FIGS. 4c/4d, the cells were treated in the absence (□) or presence of 0.3 $\mu$M (■), 1 $\mu$M (●), 3 $\mu$M (▲), 10 $\mu$M (♦), 30 $\mu$M (▼) phenylarsine oxide. TER was determined at the times indicated.

Example 4.1

PAO and pervanadate increase the paracellular flux of sucrose in MDCK cells. Sucrose flux was determined as described under Materials and Methods. Flux (mean ±S.E., n=1.6) in repsonse to 10 $\mu$M PAO, 100 $\mu$M pervanadate (PV) or 4 mM BAPTA was determined with respect to control cells (Cont.) (see FIG. 4.1).

Example 5

Pervanadate increases the tyrosine phosphorylation of many proteins in MDCK strain I cells and BBECs: comparison with the discrete effects of phenylarsine oxide. MDCK strain I cells (FIG. 5a) or cyclic AMP treated BBECs (FIG. 5b) were treated in the absence (Cont.) or presence of 100 $\mu$M pervanadate (PV) for 30 min. In FIG. 5c, MDCK strain in cells were incubated with 10 $\mu$M phenylarsine oxide for the indicated times. In FIG. 5d, cyclic AMP treated BBECs were treated with the indicated concentrations of phenylarsine oxide for 60 min. In all cases, the cells were lysed with SDS-containing buffer. Solubilised proteins were separated by SDS-PAGE and transferred to nitrocellulose. Tyrosine phosdhorylation was detected using an anti-phosyhotyrosine antibody conjugated to horseradish peroxidase followed by enhanced chemiluminescence. It should be noted that the exposure times (seconds) to obtain the results shown in FIGS. 5a and 5b were considerably shorter than those (minutes) to obtain the results in FIGS. 5c and 5d. With respect to the BBECs, similar results were obtained if the cells were treated with or without cyclic AMP.

Example 5.1

PAO increases the tyrosine phosphorylation of proteins at intercellular junctions in MDCK cells comparison with the effect of pervanadate. MDCK cells were treated in the absence (A, F) or presence of either 100 $\mu$M pervanadate for 15 (B, G) or 30 minutes (C, H) or with 10 $\mu$M PAO for 15 (D, I) or 30 minutes (E, J). The cells were stained with an anti-phosphotyrosine antibody (A-F) or an anti-E-cadherin antibody (G-J), as described under Materials and Methods, Exposure times were constant for panels A–F. Bar, 10 $\mu$m (see FIG. 5.1).

Example 5.2

PAO increases the tyrosine phosphorylation of proteins at intracellular junctions in brain endothelial cells: comparison with the effect of pervanadate. Filter-grown brain endothelial cells were treated with CPT-cAMP/Ro20-1724 for 2 days as described by Rubin et al. (1991). The cells were then incubated in the absence (A, E) or presence of either 10 $\mu$M PAO for 5 (B), 10 (C) or 30 minutes (D) or 100 $\mu$M pervanadate for 5 (F), 10 (G) or 30 minutes (H). The cells were then fixed and stained with anti-phosphotyrosine antibody as described under Materials and Methods. Exposure times were constant for panels A–D and constant, but less, for panels E—H. Bar, 20 $\mu$m (see FIG. 5.2).

Example 6

Figure 6:
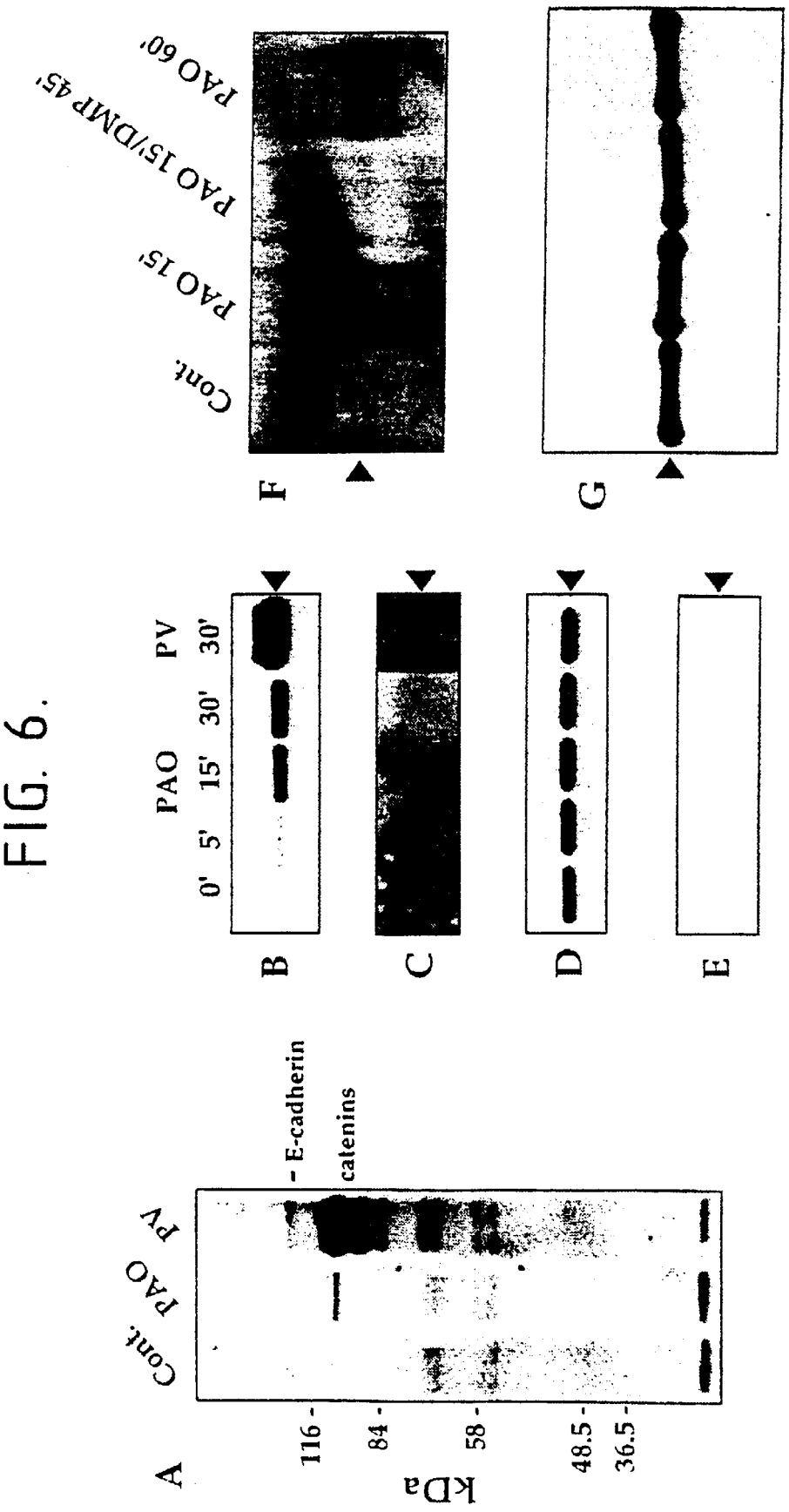
FIG. 6 shows that PAO stimulates the tyrosine phosphorylation of components of the E-cadherin/catenin complex in MDCK cells.

PAO stimulates the tyrosine phosphorylation of components of the E-cadherin/catenin complex in MDCK cells. FIG 6A: filter-grown cells were untreated (Cont.) or incubated for 30 minutes with 10 $\mu$M PAO or for 15 minutes with 100 $\mu$M pervanadate (PV). The cells were lysed in buffer containing Triton X-100 and the E-cadherin/catenin complex was immunoprecipitated using anti-E-cadherin antibody. Proteins were resolved by SDS-PAGE and tyrosine phosphorylation was detected by immunoblotting with anti-phosphotyrosine antibody. Clearly, PAO stimulates the tyrosine phosphorylation of a catenin of approximate molecular mass 100 kDa. Pervanadate stimulates the tyrosine phosphorylation of several catenins as well as E-cadherin. FIGS. 6B, C, D, E: MDCK cells were incubated with either 10 $\mu$M PAO or 100 $\mu$M pervanadate (PV) for the indicated items. The cells were lysed into denaturing buffer (containing SDS) to dissociated protein complexes and individual tyrosine phosphoproteins were immunoprecipitated using phosphotyrosine antibody. The immunoprecipitates were analyzed for either $\beta$-catenin (arrow, FIG. 6B) or $\alpha$-catenin (arrow, FIG. 6C) content by immunoblotting. Identical lysates were immunoprecipitated using peptide-directed $\alpha$-catenin antibody and blotted with the same antibody (FIG. 6D), to confirm the success of the immunoprecipitation, or phosphotyrosine antibody (FIG. 6E). Arrows indicate the migration of $\alpha$-catenin. The exposure times to obtain the negative results shown in FIGS. 6C and 6E were similar to those used to obtain the result in FIG. 6A. Clearly, the $\beta$-catenin content of the phosphotyrosine immunoprecipitates from PAO or pervanadate treated cells is increased (FIG. 6B), in contrast, the $\alpha$-catenin content is not (FIG. 6 C). Similarly, tyrosine phosphorylation (FIG. 6E) of $\alpha$-catenin immunoprecipitates (FIG. 6D) could not be detected. FIGS. 6F and 6G: MDCK cells were untreated (Cont.), incubated with 10 $\mu$M PAO for either 15 minutes and then 100 $\mu$M 2,3-dimercaptopropanol for a further 45 minutes (PAO 15'/DMP 45'). The E-cadherin/catenin immunoprecipitate was analysed by immunoblotting for phosphotyrosine (FIG. 6F) or $\alpha$-catenin content (FIG. 6G). The arrow in FIG. 6F indicates the migration of the tyrosine phosphorylated band seen in FIG. 6A. The arrow in FIG. 6G indicates the migration of $\alpha$-catenin. The tyrosine phosphorylation of the catenin is reversed by the subsequent addition of 2,3-dimercaptopropanol (FIG. 6F). The constant content of $\alpha$-catenin in the immunoprecipitates (FIG. 6G) indicates quantitatively successful immunoprecipitation in all cases.

Example 7

PAO stimulates the tyrosine phosphorylation of tight junction associated proteins in MDCK cells. MDCK cells were treated with 10 $\mu$M PAO or 100 $\mu$M pervanadate for the indicated times. The cells were lysed in buffer containing Triton X-100, SDS and sodium deoxycholate. ZO-1 and associated proteins were immunoprecipitated using ZO-1 antibody and analyzed for phosphotyrosine content by immunoblotting. Clearly, PAO treatment resulted in the tyrosine phosphorylation of ZO-1 (220 kDa). Pervanadate also stimulated tyrosine phosphorylation of ZO-1, as well as ZO-2 (160 kDa) (see FIG. 7).

Example 8

Herbimycin A attenuates the PAO-induced decrease in transcellular electrical resistance in MDCK cells. In two independent experiments, cultures were incubated in the absence or presence of the tyrosine kinase inhibitor herbimycin A (○, control; ●, 2.5 µM herbimycin A: □, control; ■, 10 µM herbimycin A) for 16–18 hours after which a resistance measurement was taken. The addition of herbimycin A alone did not affect resistance. PAO wash then added to give the final concentrations indicated and after a further 30 minutes incubation the effects on resistance were determined. The resistance values have been expressed relative to the initial values (see FIG. 8).

Example 9

Herbimycin A attenuates the PAO-induced increase in protein tyrosine phosphorylation in MDCK cells. The cultures that have been used to generate the data testing the effects of 10 µM herbimycin A in Example 8 were lysed in SDS sample buffer and separated by SDS-PAGE. Protein tyrosine phosphorylation was detected by immunoblotting using anti-phosphorylation was detected by immunoblotting using anti-phosphotyrosine antibody. HA, herbimycin A (see FIG. 9).

Example 10

Middle cerebral artery occlusion (a stroke model) elevates the levels of tyrosine phosphorylation in cells associated with small blood vessels near the area damaged by the occlusion.

Stroke model

The left middle cerebral artery of adult male Sprague-Dawley rats was exposed by craniotomy and occluded by cauterization. This gives a useful stroke model. Twenty four hours after the operation. Evan's blue (4% in PBS. 6 µl per gram body weight) was injected intravenously. After thirty minutes, the animal was anaesthetised, the blood flushed out with PBS, the brain removed and snap frozen in powdered dry ice. Sections of unfixed tissue were made using a Bright OTF cyrostat.

Evan's Blue

Sections (24 µm) were air-dried on gelatin-coated glass slides, fixed for 10 minutes in methanol at −20 ° C., washed in PBS (phosphate-buffered saline) and mounted in Citifluor.

Immunocytochemistry

Sections were air-dried and permeablised with 95% ethanol at −95° C. for 30 minutes followed by acetone at room temperature for 1 minute. All of the antibody incubations and washes used PBS containing $5 \times 10^{-4}$ M sodium vanadate. Sections were washed with PBS, blocked with 1% BSA (bovine serum albumin) for 15 minutes and incubated overnight at 4° C. with either 10 µg/ml anti-phosphotyrosine antibody (4G10) or control antibody (1:100) together with anti-collagen type IV (1:40,000). Sections were then blocked for 15 minutes in PBS/vanadate containing 1% BSA and 0.1% Triton-X100, incubated with FITC-conjugated anti-mouse IgG2b (1:100) and Texas Red-conjugated anti-rabbit Ig (1:100) for 1 hour at room temperature and mounted in Citifluor. For some sections, anti-rat albumin antibody (1:200) replaced the 4G10 antibody, and in this case FITC-conjugated anti-sheep IgG (1:100) was used instead of the anti-mouse IgG2b.

Antibodies

Anti-phosphotyrosine antibody 4G10 was from Upstate Biotechnology Inc. (TCS Biologicals, Buckingham, UK), sheep anti-rat albumin from Biogenesis (Bournemouth, UK), control mouse IgG2b from Zymed (Cambridge Bioscience, Cambridge, UK), collagen type-IV from Biogenesis, FITC-conjugated anti-mouse IgG2b from Nordic Immunological Laboratories Ltd. (Maidenhead, UK) and Texas Red-conjugated anti-rabbit Ig and FITC-conjugated anti-sheep IgG were from Jackson Immunoresearch Laboratories Inc. (Stratech, Luton, UK).

Microscopy

Sections were viewed on a Nikon Microphot FXA microscope using phase or Nomarski optics to determine morphology, and with epifluoresence to visualize the fluorophores. Excitation of Texas Red and Evan's blue was at 510–560 nm and FITC at 495 nm.

4G10 block with phosphotyrosine

4G10 antibody was incubated for 15 minutes with 3–40 mM phosphotyrosine (Sigma Chemical Company Ltd., Poole, UK) before staining the section as described above.

FIGS. 10 A, C and E: Collagen type IV, Collagen type IV is in the basement membrane around endothelial and smooth muscle cells and the antibody outlines blood vessels. FIGS. 10 B, D and F: Phosphotyrosine label of the same sections shown in FIGS. 10 A, C and E. Phosphotyrosine is not detectable in the microvessels in the normal tissue of the right cortex of an operated rat (FIG. 10 B), but is increased in vessels near the damaged area in the cortex on the left side of the same brain (FIG. 10 D). Artificial elevation of the levels of phosphotyrosine using pervanadate induces detectable levels of phosphotyrosine in both large and small vessels (FIG. 10 F (note that FIG. 10 F is inverted)).

Example 11

Characterization of anti-p120 and 2B12 immunoreactivity. Various cell lines and a primary culture of bovine brain endothelial cells (Brain EC) were lysed in SDS sample buffer and analyzed by SDS-PAGE followed by immunoblotting with anti-p120 antibody (Panel A) or the 2B12 antibody (Panel B). The exposure times were 1 minute for Panel A (apart from that for the MDBK cells which was 10 seconds) and 15 minutes for Panel B. The migration of p120 (○) and p100 (●) has been indicated (see FIG. 11).

Figure 12:
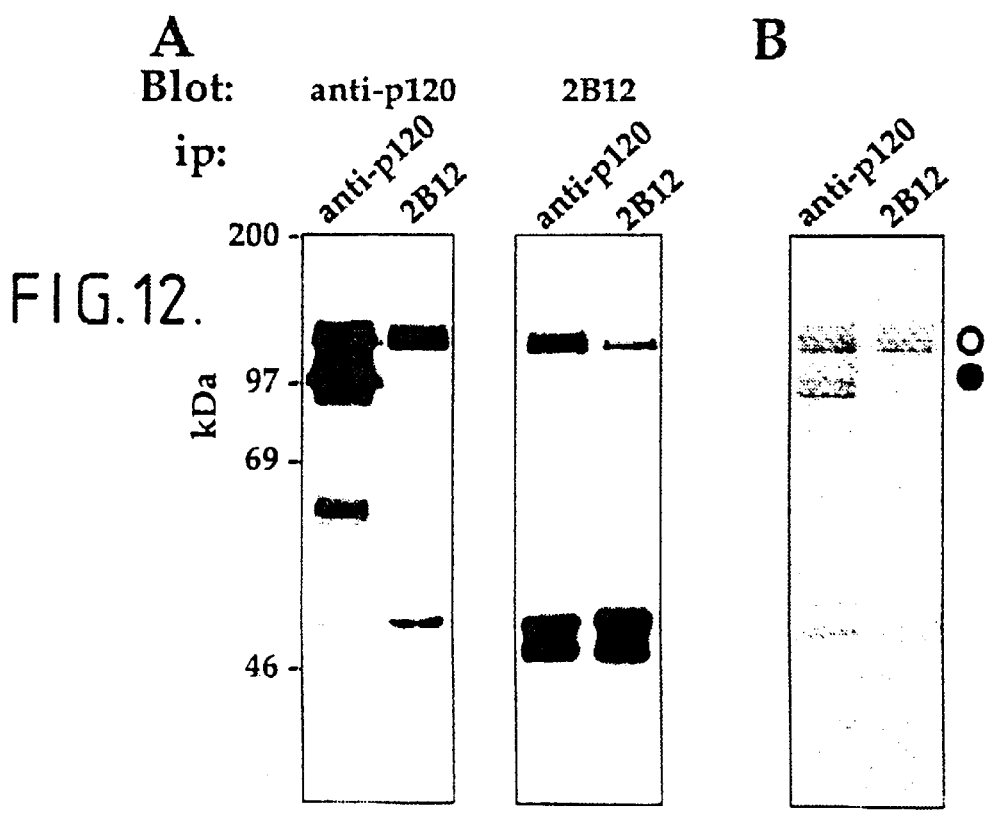
FIG. 12 shows that p120 protein is recognized by the anti-p120 antibody and cross-react with the 2B12 antibody, whereas p100 is recognized only by anti-p120.

Example 12 p120 protein is recognized by the anti-p120 antibody and cross-reacts with the 2B12 antibody, whereas p100 is recognized only by anti-p120. MDBK cells were lysed in TDS buffer. Immunoprecipitations were performed using the anti-p120 antibody or 2B12 followed by cross-blotting (Panel A). MDBK cells were chosen because p120 and p100 are well separated by SDS-PAGE and react with both antibodies. In panel B, MDBK cells were labelled with [$^{35}$S]methionine, lysed in TDS buffer and then immunoprecipitated using anti-p120 or 2B12. Proteins were separated by SDS-PAGE and detected by autoradiography. Clearly, the broad bands (Panel 12 A and see FIG. 11A) corresponding to p120 and p100 ass detected by immunoblotting are resolved as multiple bands. The same bands as seen in the 2B12 immunoprecipitate (○) are seen in the anti-p120 immunoprecipitates. In the anti-p120 immunoprecipitates, additional bands (●) corresponding to p100 are also observed (see FIG. 12).

Example 13

Comparison of anti-p120 and anti-E-cadherin immunoprecipitates from MDCK and Caco-2 cells. Panel A: MDCK cells were labelled with [$^{35}$S]methoionine and then lysed in either TX buffer or TDS buffer. Immunoprecipitations were performed using anti-p120 or anti-E-cadherin (rr1). Proteins were separated by SDS-PAGE followed by fluorography. Bands corresponding to E-cadherin (E), α-(α) and β-catenin (β) which are seen strongly in the rr1 immunoprecipitates have been indicated. The major anti-p120 reactive band migrates at approximately the position of that of p100 (see FIG. 11A). 2B12 does not appear to react with canine protein (see FIG. 11B) making positive identification of p120 difficult, Panel B: Caco-2 cells were labelled with [$^{35}$S] methionine and then lysed in TX buffer. Immunoprecipitations were performed using anti-E-cadherin (HECD-1), anti-β-catenin or anti-p120 antibodies. Proteins were separated by SDS-PAGE followed by fluorography. In all cases, four major comigrating bands were immunoprecipitated, corresponding in order of increasing mobility to E-cadherin, α-, β- and γ-catenin. (see FIG. 13).

Example 14

Detection of anti-p120 reactive material in anti-E-cadherin immunoprecipitates and E-cadherin in the anti-p120 immunoprecipitates. MDCK cells were lysed in TX buffer. Immunoprecipitations were performed with either antibody to E-cadherin (rr1), the anti-p120 antibody or anti-focal adhesion kinase (anti-FAK). A sham immunoprecipitation was performed in the absence of primary antibody (−). Following separation by SDS-PAGE, parallel blots were probed using: rr1 (arrowhead, E-cadherin); anti-β-catenin (arrowhead, β-catenin); anti-p120 (arrowhead, anti-p120 reactivity); anti-FAK (arrowhead, FAK). Clearly, rr1 and the anti-p120 antibody immunoprecipitate E-cadherin and β-catenin. rr1 could also immunoprecipitate anti-p120 immunoreactive material, but to a lesser extent than that immunoprecipitated by the anti-p120 antibody. Anti-FAK could only immunoprecipitate FAK, and the sham immunoprecipitation did not result in any detectable E-cadherin, β-catenin or anti-p120 reactive material (see FIG. 14).

Example 15

Comparison of anti-β-catenin, anti-p120 and 2B12 immunoprecipitates from primary cultures of bovine brain endothelial cells. Cells were labelled with [$^{35}$S]methionine and then lysed in TX buffer or TDS buffer. Immunoprecipitations were performed using anti-β-catenin, anti-p120 and 2B12. Proteins were separated by SDS-PAGE followed by fluorography. In the β-catenin immunoprecipitation from TX lysed cells, bands corresponding to a cadherin (C), α-catenin (α) and β-catenin (β) have been indicated. Under TDS conditions, a band (○) corresponding to p120 is seen in the anti-p120 and 2B12 immunoprecipitates and a further band (●) is only seen in the anti-p120 immunoprecipitate, corresponding to p100 (see FIG. 15).

Example 16

Detection of p120/p100 in β-catenin immunoprecipitates and β-catenin in anti-p120 immunoprecipitates from human umbilical vein endothelial cells (Panel A) and ECV304 cells (Panel B). Cells were lysed in either TX or TDS buffer. Lysates were immunoprecipitated using anti-β-catenin or the anti-p120 antibody, followed by analysis by SDS-PAGE and immunoblotting. The migration of β-catenin (arrowheads), p100 (●) and p120 (○) have been indicated. Note the absence of anti-p120 reactive material in the β-catenin immunoprecipitates obtained using TDS buffer. Even though β-catenin and p100, as defined by its reactivity with anti-p120 antibody, migrate very closely, they are clearly distinct proteins (see FIG. 16).

Example 17

Localization of anti-p120 reactivity and β-catenin in MDCK cells, and brain endothelial cells. MDCK cells (Panel a,b) and porcine brain endothelial cells (Panel c,d) were co-labelled with anti-p120 antibody (Panel a,c) and anti-β-catenin antibody (Panel b,d). Secondary antibodies were fluorescein-conjugated anti-mouse and rhodamine-conjugated anti-rabbit. In this instance, it was verified that each secondary antibody was absolutely specific for its designated species of primary antibody. Bar: 20 μm (See FIG. 17).

Example 18

Distribution of anti-p120 immunoreactivity in brain and skeletal muscle tissue of the rat. Brain tissue was co-labelled with the anti-p120 antibody (a,c) and anti-α-catenin (b,d). Anti-p120 immunoreactivity and α-catenin co-locaiise at intercellular junction of choroid plexus epithelium (arrows, a and b) and ventrical ependymal cells (arrowheads, a and b). Both antigens also co-locaiise at interendothelial junctions of blood vessels of macrovascular origin (arrows in c and d). Microvascular profiles in brain sections were identified by labelling with anti-collagen IV antibody (f); co-labelling with the anti-p120 antibody (e), revealed the presence of anitgen at interendothelial junctions (e, arrows). In these microvessels, α-catenin co-localised with anti-p120 immunoreactivity (not shown). In muscle tissue which had been cut perpendicular to the orientation of the muscle fibres, anti-p120 immunoreactivity is limited to areas between muscle fibres where blood vessels are located (g, arrows). Higher magnification reveals a punctate staining pattern (h, arrows) which is likely to reflect anti-p120 immunoreactivity at interendothelial junctions. In Panels a,c and e, bp depicts the brain parenchyma; in Panel a,v the ventrical lumen and cp the choroid plexus; in Panel g, m refers to muscle tissue. Bars: (a, g), 100 μm; (c, e, h), 25 μm (see FIG. 18).

Example 19

Sequence analysis of peptides derived by LysC proteolysis of p100 from Caco-2 cells. Caco-2 cells (20×confluent 9 cm dishes) were lysed in TX buffer to minimize nuclear lysis. Insoluble protein was removed by centrifugation. Deoxycholate and SDS were added to the supernatant to give (w/v) 0.5% and 0.2% final concentration, respectively. Addition of these detergents results in dissociation of p100 and p120 from the cadherin/catenin complex. p120 and p100 were immunoprecipitated from the lysate using the anti-p120 antibody (which also recognizes p100) from Transduction Laboratories, rabbit anti-mouse IgG and Protein A Sepharose. The immune complex was washed five times and then dissociated by the addition of Laemmli sample buffer followed by heating at 100° C. for 5 minutes. Proteins were precipitated by addition of four volumes of ethanol and incubation at −20° C. for 16 hours. The precipitate was resolved by SDS-PAGE (6% acrylamide) and proteins were visualized by Coomassie Blue. Protein corresponding to p100 was excised from the gel and digested with LysC. Peptides were separated by HPLC and sequenced (SEQ ID NO: F9). Mouse p120 sequence was described by Reynolds et al., 1992. Clearly, human p100 is closely related to mouse p120 (SEQ ID NO: 519).

The following reference list gives details of the articles referred to herein.

Anderson J. M., Balda, M. S., and Fanning, A. S. (1993). The structure and regulation of tight junctions. *Curr. Opin. Cell Biol.* 5, 772–778.

Balda, M. S., and Anderson J. M. (1993). Two classes of tight junctions are revealed by ZO-1 isoforms. *Am. J. Physiol.* 264, C918–C924.

Balda M. S., Gonzalez-Mariscal, L., Matter, K., Cereijido, M. and Anderson, J. M. (1993). Assembly of the tight junction: the role of diacylglycerol. *J. Cell Biol.* 123, 293–302.

Behrens, J., Vakaet, L., Friis, R., Winterhager, E., Van Roy, F., Mareel, M. M. and Birchmeier, W. (1993). Loss of epithelial differentiation and gain of invasiveness correlate with tyrosine phosphorylation of the E-cadherin/β-catenin complex in cells transformed with a temperature-sensitive v-SRC gene. *J. Cell Biol.* 120, 757–766.

Bernier, M., Laird, D. M. and Lane, M. D. (1987). Insulin-activated tyrosine phosphorylation of a 15-kilodalton protein in intact 3T3-L1 adipocytes. *Proc. Nat. Acad. Sci. USA* 84, 1844–1848.

Butz, S., Stappert, J., Weissig, H. and Kemler, R. (1992). Plakoglobin and beta-catenin: distinct but closely related. *Science* 257, 1142–1144.

Citi, S., Sabanay, H., Jakes, R., Geiger, B. and Kendrick-Jones J. (1988). Cingulin, a new peripheral component of tight junctions. *Nature* 333, 272–276.

Citi, S. (1992). Protein kinase inhibitors prevent junction dissociation induced by low extracellular calcium in MDCK epithelial cells. *J. Cell Biol.* 117, 169–178.

Citi, S. (1993). The molecular organization of tight junctions. *J. Cell Biol.* 121, 485–489.

Fantus, I. G., Kadota, S., Deragon, G., Foster, B. and Posner, B. I. (1989). Pervanadate [peroxides(s) of vanadate] mimics insulin action in rat adipocytes via activation of the insulin receptor tyrosine kinase. *Biochemistry* 28, 8864–8871.

Furuse, M., Hirase, T., Itoh, M., Nagafuchi, A., Yonemura, S., Tsukita, S. and Tsukita, S. (1993). Occludin: A novel integral membrane protein localizing at tight junctions. *J. Cell Biol.* 123, 1777–1788.

Garcia-Morales, P., Mianmi, Y., Luong, E., Klausner, R. D. and Samelson, L. E. (1990). Tyrosine phosphorylation in T cells is regulated by phosphatase activity: studies with phenylarsine oxide. *Proc. Nat. Acad. Sci. USA* 87, 9255–9259.

Geiger, B., and Ayalon, O. (1992). Cadherins. *Annu. Rev. Cell Biol.* 8, 307–332.

Gumbiner, B. (1987). Structure, biochemistry, and assembly of epithelial tight junctions. *Am. J. Physiol.* 253, C749–C758.

Gumbiner, B., and Simons, K. (1986). A functional assay for proteins involved in establishing an epithelial occluding barrier: identification of a uvomorulin-like polypeptide. *J. Cell Biol.* 102, 457–468.

Gumbiner, B., Stevenson, B. and Grimaldi, A. (1988). The role of the cell adhesion molecule uvomorulin in the formation and maintenance of the epithelial junctional complex. *J. Cell Biol.* 107, 1576–1587.

Gumbiner, B., Lowenkopf, T., and Apatira, D. (1991). Identification of a 160-kDa polypeptide that binds to the tight junction protein ZO-1. *Proc. Nat. Adad. Sci. USA* 88, 3460–3464.

Hamaguchi, M., Matsuyoshi, N., Ohnishi, Y., Gotoh, B., Takeichi, M. and Nagai, Y. (1993). p60$^{v-src}$ causes tyrosine phosphorylation and inactivation of the N-cadherin-catenin cell adhesion system. *EMBO J.* 12, 307–314.

Heffetz, D., Bushkin, I., Dror, R. and Zick Y. (1990). The insulinomimetic agents $H_2O_2$ and vanadate stimulate protein tyrosine phosphorylation in intact cells. *J. Biol. Chem.* 265, 2896–2902.

Herrenknecht, K., Ozawa, M., Eckerskorn, C., Lottspeich, F., Lenter M. and Kemler, R. (1991). The uvomorulin-anchorage protein alpha catenin is a vinculin homologue. *Proc. Nat. Acad. Sci. USA* 88, 9156–9160.

Hirano, S., Nose, A., Hatta, K., Kawakami, A. and Takeichi, M. (1987). Calcium-dependent cell-cell adhesion molecules (cadherins): subclass specificities and possible involvement of actin bundles. *J. Cell Biol.* 105, 2501–2510.

Kintner, C. (1992). Regulation of embryonic cell adhesion by the cadherin cytoplasmic domain. *Cell* 69, 225–236.

Laemmli, U. K. (1970). Cleavage of structural proteins during the assembly of the head of bacteriophage T4. *Nature* 227, 680–685.

Langeler, E. G., and Van Hinsberg, V. W. M. (1991). Norepinephrine and iloprost improve barrier function of human endothelial cell monolayers: role of cAMP. *Am. J. Physiol.* 260, C1052–C1059.

Levenson, R. M., and Blackshear, P. J. (1989). Insulin-stimulated protein tyrosine phosphorylation in intact cells evaluated by giant two-dimensional gel electrophoresis. *J. Biol. Chem.* 264, 19984–19993.

Madara, J. L. (1988). Tight junction dynamics: is paracellular transport regulated? *Cell* 53, 497–498.

Martinez-Palomo, A., Meza, I., Beaty, G. and Cereijido, M. (1980). Experimental modulation of occluding junctions in a cultured transporting epithelium. *J. Cell Biol.* 87, 736–745.

Matsuyoshi, N., Hamaguci, M., Taniguchi, S., Nagafuchi, A., Tsukita, S. and Takeichi M. (1992). Cadherin-mediated cell-cell adhesion is perturbed by v-src tyrosine phosphorylation in metastatic fibroblasts. *J. Cell Biol.* 118, 703–714.

Nagafuchi, A. and Takeichi, M. (1988). Cell binding function of E-cadherin is regulated by the cytoplasmic domain. *EMBO J.* 7, 3679–3684.

Nagafuchi, A., Takeichi, M. and Tsukita, S. (1991). The 102 kDa cadherin-associated protein: similarity to vinculin and posttranscriptional regulation of expression. *Cell* 65, 849–857.

Ojakian, G. (1981). Tumor promoter-induced changes in the permeability of epithelial tight junctions. *Cell* 25, 95–103.

O'Shea, J. J., McVicar, D. W., Bailey, T. L., Burns, C. and Smith M. J. (1992). Activation of human peripheral blood T lymphocytes by pharmacological induction of protein-tyrosine phosphorylation. *Proc. Nat. Acad. Sci. USA* 89, 10306–10310.

Ozawa, M., Baribault, H. and Kemler, R. (1989). The cytoplasmic domain of the cell adhesion molecule uvomorulin associates with three independent proteins structurally related in different species. *EMBO J.* 8, 1711–1717.

Ozawa, M., Ringwald, M. and Kemler, R. (1990). Uvomorulin-catenin complex formation is regulated by a specific domain in the cytoplasmic region of the cell adhesion molecule. *Proc. Nat. Acad. Sci. USA* 87, 4246–4250.

Parkos, C. A., Coglan, S. P., Delp, C., Arnout, M. A. and Madara J. L. (1992). Neutrophil migration across a cultured epithelial monolayer elicits a biphasic resistance response representing sequential effects on transcellular and paracellular pathways. *J. Cell Biol.* 117, 757–764.

Pronk, G. J., Medema, R. H., Burgering, R. M. T., Clark, R., McCormick, F. and Bos, J. L. (1992). Interaction between the p21$^{ras}$ GTPase activating protein and the insulin receptor. *J. Biol Chem.* 267, 24058–24063.

Rodriguez-Boulan, E., and Nelson, W. J. (1989). Morphogenesis of the polarized epithelial cell phenotype. *Science* 245, 718–725.

Rubin, L. L., Hall, D. E., Porter, S., Barbu, K., Cannon, C., Horner, H. C., Jantapour, M., Liaw, C. W., Manning, K., Morales, J., Tanner, L. I., Tomaselli, K. J. and Bard F. (1991). A cell culture model of the blood-brain barrier. *J. Cell Biol.* 115, 1725–1735.

Rubin, L. (1992). Endothelial cells:adhesion and tight junctions. *Curr. Opin. Cell Biol.* 4, 830–833.

Rutten, M. J., Hoover, R. L. and Karnovsky, M. J. (1987). Electrical resistance and macromolecular permeability of brain endothelial monolayer cultures. *Brain Res.* 425, 301–310.

Stappert, J., and Kemler, R. (1993). Intracellular associations of adhesion molecules. *Curr. Opin. Neurobiol.* 3, 60–66.

Stelzner, T. J., Weil, J. V. and O'Brien, R. F. (1989). Role of cyclic adenosine monophosphate in the induction of endothelial barrier properties. *J. Cell. Physiol.* 139, 157–166.

Stevenson, B. R., Siciliano, J. D., Mooseker, M. S. and Goodenough, D. A. (1986). Identification of ZO-1: a high molecular weight polypeptide associated with the tight junction (zonula occludens) in a variety of epithelia. *J. Cell Biol.* 103, 755–766.

Stevenson, B. R., Anderson, J. M., Goodenough, D. A. and Mooseker, M. S. (1988). Tight junction structure and ZO-1 content are identical in two strains of Madin-Darby canine kidney cells which differ in transepithelial resistance. *J. Cell Biol.* 107, 2401–2408.

Stevenson, B. R., Anderson, J. M., Braun, I. D. and Mooseker, M. S. (1989). Phosphorylation of the tight-junction protein ZO-1 in two strains of Madin-Darby canine kidney cells which differ in transepithelial resistance. *Biochem. J.* 263, 597–599.

Tsukita S., Oishi, K., Akiyama, T., Yamanishi, Y., Yamamoto, T. and Tsukita, S. (1991). Specific proto-oncogenic tyrosine kinases of src family are enriched in cell-to-cell adherens junction where the level of tyrosine phosphorylation is elevated. *J. Cell Biol.* 113, 867–879.

Volberg, T., Geiger, B., Dror, R. and Zick, Y. (1991). Modulation of intercellular adherens-type junctions and tyrosine phosphorylation of their components in RSV-transformed cultured chick lens cells. *Cell Regulation* 2, 105–120.

Volberg, T., Zick, Y., Dror, R., Sabanay, I., Gilon, C., Levitzki, A. and Geiger, B. (1992). The effect of tyrosine-specific protein phosphorylation on the assembly of adherens-type junction. *EMBO J.* 11, 1733–1742.

Warren, S. L. and Nelson, W. J. (1987). Nonmitogenic morphoregulatory action of pp60$^{v-src}$ on multicellular epithelial structures. *Mol. Cell. Biol.* 7, 1326–1337.

Willott, E., Balda, M. S., Heintzelman, M., Jameson, B. and Anderson J. M. (1992). Localization and differential expression of two isoforms of the tight junction protein ZO-1. *Am. J. Physiol.* 262, C1119–C1124.

Willott, E., Balda, M. S., Fanning, A. S., Jameson, B., van Itallie, C. and Anderson, J. M. (1993). The tight junction protein ZO-1 is homologous to the Drosophila discs-large tumor suppressor protein of septate junctions. *Proc. Nat. Acad. Sci. USA* 90, 7834–7838.

Zhong, Y., Saitoh, T., Minase, T., Sawada, N., Enomoto, K. and Mori, M. (1993). Monoclonal antibody 7H6 reacts with a novel tight-junction associated protein distinct from ZO-1, cingulin and ZO-2. *J. Cell Biol.* 120, 477–483.

Behrens, J., M. M. Mareel, F. M. Van Roy, and W. Birchmeier. 1989. Dissecting tumor cell invasion: epithelial cells acquire invasive properties after the loss of uvomorulin-mediated cell-cell adhesion. *J. Cell Biol.* 108:2435–2447.

Birchmeier, W., and J. Behrens. 1994. Cadherin expression in carcinomas: role in the formation of cell junctions and the prevention of invasiveness. *Biochim. Biophys. Acta.* 1198:11–26.

Boller, K., D. Vestweber, and R. Kemler. 1985. Cell-adhesion molecule uvomorulin is localized in the intermediate junctions of adult intestinal epithelial cells. *J. Cell Biol.* 100:327–332.

Downing, J. R., and A. B. Reynolds. 1991. PDGF, CSF-1, and EGF induce tyrosine phosphorylation of p120, a pp60$^{src}$ transformation-associated substrate. *Oncogene.* 6:607–613.

Durieu-Trautmann, O., C. Fédérici, C. Créminon, N. Foignant-Chaverot, F. Roux, M. Claire, A. D. Strosberg and P. O. Couraud. 1993. Nitric oxide and endothelin secretion by brain microvessel endothelial cells: regulation by cyclic nucleotides. *J. Cell. Physiol.* 155: 104–111.

Franke, W. W., M. D. Goldschmidt, R. Zimbelmann, H. M. Mueller, D. L. Schiller, and P. Cowin. 1989. Molecular cloning and amino acid sequence of human plakoglobin, the common junctional plaque protein. *Proc. Natl. Acad. Sci. USA.* 86:4027–4031.

Frixen, U. H., Behrens, M. Sachs, G. Eberle, B. Voss, A. Warda, D. Lochner, W. Birchmeier. 1991. E-cadherin-mediated cell-cell adhesion prevents invasiveness of human carcinoma cell. *J. Cell Biol.* 113:173–185.

Hatzfield, M., G. I. Kristijansson, U. Plessmann, and K. Weber. 1994. Band 6 protein, a major constituent of desmosomes from stratified epithelia, is a novel member of the *armadillo* gene family. *J. Cell Sci.* 107:2259–2270.

Hedrick, L., K. R. Cho, and B. Vogelstein. 1993. Cell adhesion molecules as tumour suppressors. *Trends Cell Biol.* 3:36–39.

Hirano, S., N. Kimoto, Y. Shimoyama, S, Hirohashi, and M. Takeichi. 1992. Identification of neutral α-catenin as a key regulator of cadherin function and multicellular organization. *Cell* 70:293–301.

Kanner, S. B., A. B. Reynolds, R. R. Vines, and J. T. Parsons. 1990. Monoclonal antibodies to individual tyrosine-phosphorylated protein substrates of oncogene-encoded tyrosine kinases. *Proc. Natl. Acad. Sci. USA.* 87:3328–3332.

Kanner S. B., A. B. Reynolds, and J. T. Parsons. 1991. Tyrosine phosphorylation of a 120-kilodalton pp60$^{src}$ substrate upon epidermal growth factor and platelet-derived growth factor receptor stimulation and in polyomavirus middle-T-antigen-transformed cells. *Mol. Cell Biol.* 11:713–720.

Kikuchi, A. K., Kaibuchi, Y. Hori, H. Nonaka, T. Sakoda, M. Kawamura, T. Mizuno, and Takai, Y. 1992. Molecular cloning of the human cDNA for a stimulatory GDP/GTP exchange protein for c-Ki-ras p21 and smg p21. *Oncogene.* 7:289–293.

Kinzler, K. W., M. C. Nilbert, L. Su, B. Vogelstein, T. M. Bryant, D. B. Levy, K. Smith, A. C. Preisinger, P. Hedge, D. McKechnie, R. Finnear, A. Markham, J. Groeffen, M. S. Boguski, S. F. Altschul, A. Hortii, H. Ando, Y. Miyoshi, Y. Miki, I. Nishisho, and Y. Nakamura. 1991. Identification of FAP Locus genes from chromosomes 5q21 *Science,* 253:661–665.

Knudsen, K. A., and M. J. Wheelock. 1992. Plakoglobin, or an 83-kD homologue distinct from β-catenin, interacts with E-cadherin and N-cadherin. *J. Cell Biol.* 1992. 118:671–679.

Linder, M. E., and J. G. Burr. 1988. Nonmyristoylated p60$^{v-src}$ fails to phosphorylate proteins of 115–120 kDa in chicken embryo fibroblasts. *Proc. Natl. Acad. Sci. USA.* 83:2608–2612.

Matsuzaki, F., Mege, R. M., S. H. Jaffe, D. R. Friedlander, W. J. Gallin, J, I, Goldberg, B. A. Cunningham, and G. M. Edelman, 1990. cDNAs of cell adhesion molecules of different specificity induce changes in cell shape and border formation in cultured S180 cells. *J. Cell Biol.* 110:1239–1252.

McCrea, P. D., and B. M. Gumbiner. 1991. Purification of a 92-kDa cytoplasmic protein tightly associated with the cell-cell adhesion molecule E-cadherin (uvomorulin). Characterization and extractability of the protein complex from the cell cytostructure. *J. Biol. Chem.* 266:4515–4520.

McCrea, P. D., C. W. Turck, and B. Gumbiner. 1991. A homolog of the *armadillo* protein in Drosophila (plakoglobin) associated with E-cadherin. *Science.* 254:1359–1361.

Musil, L. S., Cunningham, B. A., Edelman, G. M., and D. Goodenough. 1990. Differential phosphorylation of the gap junction protein connexin43 in junctional communication-competent and -deficient cell lines. *J. Cell Biol.* 111:2077–2088.

Nelson W. J. 1992. Regulation of cell surface polarity from bacteria to mammals. *Science.* 258:948–955.

Peifer, M., and E. Wieschaus. 1990. The segment polarity gene *armadillo* encodes a functionally modular protein that is the Drosophila homolog of human plakoglobin. *Cell.* 63:1167–1176.

Peifer, M., P. D. McCrea, K. J. Green, E. Wieschaus, and B. M. Gumbiner. 1992. The vertebrate adhesive junction proteins β-catenin and plakoglobin and the Drosophila segment polarity gene *armadillo* form a multigene family with similar properties. *J. Cell Biol.* 118:681–691.

Peifer, M., S. Berg,. and A. B. Reynolds. 1994. A repeating amino acid motif shared by proteins with diverse cellular roles. *Cell.* 76:789–91.

Piepenhagen, P. A., and W. J. Nelson. 1993. Defining E-cadherin-associated protein complexes in epithelial cells: plakoglobin, beta- and gamma- catenin are distinct components. *J. Cell Sci.* 104:751–762.

Reynolds, A. B., D. J. Roesel, S. B. Kanner, and J. T. Parsons. 1989. Transformation-specific tyrosine phosphorylation of a novel cellular protein in chicken cells expressing oncogenic variants of the Avian cellular src Gene. *Mol. Cell Biol.* 9:629–638.

Reynolds, A. B., L. Herbert, J. L. Cleveland, S. T. Berg, and J. R. Gaut. 1992. p120, a novel substrate of protein tyrosine kinase receptors and of p60$^{v-src}$, is related to cadherin-binding factors beta-catenin, plakoglobin and armadillo. *Oncogene.* 7:2439–2445.

Riggleman, B., E. Wieschaus, and R. Schedl. 1989. Molecular analysis of the *armadillo* locus: uniformly distributed transcripts and a protein with novel internal repeats are associated with a Drosophila segment polarity gene. *Genes Dev.* 3:96–113.

Rubinfeld, B., B. Souza, I. Albert, O. Muller, S. H. Chamberlain, R. H. Masiarz, S. Munemitsu, and P. Polakis. 1993. Association of the APC gene product with β-catenin. *Science.* 262:1731–1724.

Shimoyama, Y., S. Hirohashi, S. Hirano, M. Noguchi, Y. Shimosato, M. Takeichi and O. Abe. 1989. Cadherin cell-adhesion molecules in human epithelial tissues and carcinomas. *Cancer Res.* 49: 2128–2133.

Shimoyama, Y., A. Nagfuchi, S. Fujita, M. Gotoh, M. Takeichi, S. Tsukita, and S. Hiroshashi. 1992. Cadherin dysfunction in a human cancer cell line: possible involvement of loss of α-catenin expression in reduced cell-cell adhesiveness. *Cancer Res.* 52:1–5.

Staddon, J. M., K. Herrenknecht, C. Smales, and L. L. Rubin. Evidence that tyrosine phosphorylation may increase tight junction permeability. *J. Cell Sci.* in press.

Su, L. K., B. Vogelstein, and K. W. Kinzler. 1993. Association of the APC tumor suppressor protein with catenins. *Science.* 262:1734–1737.

Takeichi, M. 1991. Cadherin cell adhesion receptors as morphology regulators. *Science.* 251:1451–1455.

Tsukita, S., M. Itoh, A. Nagafuchi, and S. Yonemura. 1993. Submembranous junctional plaque proteins include potential tumour suppressor molecules. *J. Cell Biol.* 123:1049–1053.

Vleminckx, K., L. Vakaet, M. Jr. Mareel, W. Fries, and F. Van Roy. 1991. Genetic manipulation of E-cadherin expression by epithelial tumor cells reveals an invasion suppressor role. *Cell* 66:107–119.

Yano, R., M. L. Oakes, M. Yamaghishi, J. A. Dodd, and M. Nomura. 1992. Cloning and characterization of SRP1, a suppressor of temperature-sensitive RNA polymerase I mutations, in *Saccharomyces cerevisiae. Mol. Cell. Biol.* 12:5640–5651.

Yano, R., M. L. Oakes, M. M. Taub, and M. Nomura. 1994. Yeast srp1p has homology to armadillo/plakoglobin/β-catenin and participates in apparently multiple nuclear functions including the maintenance of the nucleolar structure. *Proc. Natl. Acad. Sci. USA* 91:6880–6884.

What is claimed is:

1. A method for reducing permeability of a physiological barrier comprising adherens junctions and/or tight junctions in a first subject suffering from a central nervous system (CNS) disorder or other disorder, wherein said CNS or other disorder is characterized by increased permeability of a physiological barrier relative to the permeability of said barrier in a second subject not suffering from said CNS or other disorder, wherein said CNS or other disorder is characterized by increased permeability of said physiological barrier due to enhanced tyrosine phosphorylation, said method comprising administering to said first subject an effective amount of an agent which promotes tyrosine protein dephosphorylation of at least one component of a cadherin/catenin complex in said adherens junctions and/or tight junctions.

2. The method of claim 1, wherein the agent directly or indirectly inhibits tyrosine protein kinase.

3. The method of claim 1, wherein said physiological barrier comprises an inter-endothelial cell tight junction.

4. The method of claim 3, wherein said physiological barrier is in the blood-brain barrier.

5. The method of claim 1, wherein said subject is a mammal.

6. The method of claim 5, wherein said mammal is a human.

7. The method of claim 1, wherein the agent directly or indirectly activates tyrosine protein phosphatase.

8. The method of claim 1, wherein the dephosphorylation promotion effect of the agent is reversible or sufficiently reversible to avoid untoward toxicity problems.

9. The method of claim 1, wherein said component of the cadherin/catenin complex is a cadherin selected from the group consisting of:

i) E-cadherin
ii) N-cadherin and
iii) P-cadherin.

10. The method of claim 1, wherein said component of the cadherin/catenin complex is a component selected from the group consisting of:

i) β-catenin
ii) ZO-1
iii) ZO-2
iv) p100 and
v) p120.

11. The method of claim 1, wherein said CNS disorder is selected from the group of CNS disorders consisting of multiple sclerosis, stroke, a CNS tumour, a CNS oedema.

12. The method of claim 1, wherein said other disorders selected from the group of disorders consisting of cancer matastasis, pulmonary oedema, accumulation of mucous in the pulmonary airways, and gastric ulcer.

13. A method for reducing permeability of adherens junctions and/or tight junctions in a first subject suffering from a central nervous system (CNS) disorder or other disorder, wherein said CNS or other disorder is characterized by increased permeability of adherens junctions and/or tight junctions due to enhanced tyrosine phosphorylation, relative to the permeability of said junctions in a second subject not suffering from CNS or other disorder, said method comprising administering to said first subject an effective amount of an agent which promotes tyrosine protein dephosphorylation of at least one component of a cadherin/catenin complex in said adherens junctions and/or tight junctions.

* * * * *